(12) United States Patent
Olson et al.

(10) Patent No.: US 12,740,852 B2
(45) Date of Patent: Sep. 22, 2026

(54) STENT WITH ANTI-MIGRATION FEATURES

(71) Applicant: BOSTON SCIENTIFIC SCIMED, INC., Maple Grove, MN (US)

(72) Inventors: Mark Phillip Olson, New Brighton, MN (US); Raymond David Gessler, III, Roberts, WI (US); Matthew Maciej, Rogers, MN (US); Nathan Stenger, St. Paul, MN (US); Danielle Frankson, Dayton, MN (US); David Robert Wulfman, Minneapolis, MN (US); Kurt Nicholas Robakiewicz, Upton, MA (US); Ryan V. Wales, Northborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 250 days.

(21) Appl. No.: 18/501,832

(22) Filed: Nov. 3, 2023

(65) Prior Publication Data

US 2024/0148487 A1 May 9, 2024

Related U.S. Application Data

(60) Provisional application No. 63/422,519, filed on Nov. 4, 2022.

(51) Int. Cl.
*A61F 2/04* (2013.01)
*A61F 2/00* (2006.01)

(52) U.S. Cl.
CPC ........ *A61F 2/04* (2013.01); *A61F 2002/0081* (2013.01); *A61F 2002/041* (2013.01);
(Continued)

(58) Field of Classification Search
CPC ................ A61F 2/04; A61F 2002/0081; A61F 2002/041; A61F 2210/0076;
(Continued)

(56) References Cited

U.S. PATENT DOCUMENTS 4,604,762 A 8/1986 Robinson
7,914,568 B2 3/2011 Cully et al.
(Continued)

FOREIGN PATENT DOCUMENTS

CN 110946675 A * 4/2020 .............. A61F 2/90
JP S62127489 A 6/1987
(Continued)

OTHER PUBLICATIONS

Domingues, B., Silva, J.M., Aroso, I.M., Lima, E., Barros, A.A., Reis, R.L. (2022). Coatings for Urinary Stents: Current State and Future Directions. In: Soria, F., Rako, D., de Graaf, P. (eds) Urinary Stents. Springer, Cham. https://doi.org/10.1007/978-3-031-04484-7_18 (Year: 2022).*
(Continued)

*Primary Examiner* — Susan S Su
(74) *Attorney, Agent, or Firm* — Seager, Tufte & Wickhem, LLP

(57) ABSTRACT

Stents and/or endoluminal implants for extending across two non-adherent structures/tissues. An illustrative stent may comprise an elongated tubular body having a scaffolding forming a plurality of cells and a coating disposed over an outer surface of the elongated tubular body. The coating may comprise a first micro-porous layer and a macro-porous layer including a plurality of loops disposed over the micro-porous layer.

20 Claims, 17 Drawing Sheets

(52) U.S. Cl.
CPC ................. *A61F 2210/0076* (2013.01); *A61F 2250/0059* (2013.01)

(58) Field of Classification Search
CPC ................ A61F 2250/0059; A61F 2/07; A61F 2002/072; A61F 2/848; A61F 2/90; A61F 2250/0023; A61F 2250/0031; A61F 2250/0051; A61B 2017/00526; A61B 2017/00964; A61B 2017/1139; A61B 17/1114
See application file for complete search history.

(56) References Cited

U.S. PATENT DOCUMENTS

| | | | | |
|---|---|---|---|---|
| 8,585,753 | B2 | 11/2013 | Scanlon et al. | |
| 8,734,829 | B2 | 5/2014 | Weber | |
| 8,915,952 | B2 | 12/2014 | Rudakov | |
| 11,129,618 | B2 | 9/2021 | Sander et al. | |
| 11,160,960 | B2 | 11/2021 | Gray et al. | |
| 2005/0137675 | A1 | 6/2005 | Dubson et al. | |
| 2007/0255388 | A1* | 11/2007 | Rudakov | A61F 2/07 623/1.11 |
| 2008/0082177 | A1* | 4/2008 | Yang | A61F 2/0045 623/23.75 |
| 2009/0048659 | A1 | 2/2009 | Weber et al. | |
| 2011/0030885 | A1* | 2/2011 | Anneaux | A61F 2/07 156/187 |
| 2013/0122248 | A1 | 5/2013 | Haselby et al. | |
| 2013/0190856 | A1 | 7/2013 | Von Oepen et al. | |
| 2015/0051693 | A1 | 2/2015 | Bertolino et al. | |
| 2016/0296351 | A1 | 10/2016 | Ballard et al. | |
| 2019/0076274 | A1 | 3/2019 | Hingston et al. | |
| 2019/0151081 | A1* | 5/2019 | Limem | A61L 27/38 |
| 2020/0030124 | A1 | 1/2020 | Bluecher et al. | |
| 2021/0068994 | A1 | 3/2021 | Sanders et al. | |
| 2021/0275177 | A1 | 9/2021 | Binmoeller et al. | |
| 2021/0322629 | A1 | 10/2021 | Lydecker et al. | |
| 2022/0016401 | A1 | 1/2022 | Gray et al. | |
| 2022/0047783 | A1 | 2/2022 | Hall et al. | |
| 2022/0048285 | A1 | 2/2022 | Hall et al. | |
| 2022/0054252 | A1 | 2/2022 | Eller et al. | |
| 2022/0079784 | A1 | 3/2022 | Folan | |
| 2022/0192670 | A1 | 6/2022 | Fleury et al. | |
| 2022/0296396 | A1 | 9/2022 | Wulfman et al. | |

FOREIGN PATENT DOCUMENTS

| | | | | |
|---|---|---|---|---|
| JP | 2007530213 | A | 11/2007 | |
| JP | 2010536431 | A | 12/2010 | |
| JP | 2014204808 | A * | 10/2014 | A61L 27/00 |

OTHER PUBLICATIONS

Dolmatch, B. (2025). The Evolution of Covered Stents for Hemodialysis Access. Supplement to Endovascular Today, Aug. 2025 vol. 24, No. 8 (Year: 2025).*

VacStent GI Colon (2026) https://emea.mtmed.com/en/gastroenterology/nitinol-stents/colonic-and-rectal/vac-stent-gi-colon/ (Year: 2026).*

Coulter et al., “Additive Manufacturing of Multi-Scale Porous Soft Tissue Implants that Encourage Vascularization and Tissue Ingowth,” Advanced Healthcare Materials, vol. 10, Issue 14, 16 pages, 2021.

Zhu et al., “Mesh Implants: An Overview of Crucial Mesh Parameters,” World Journal of Gastrointestinal Surgery, vol. 7, No. 10, pp. 226-236, Oct. 27, 2015.

U.S. Appl. No. 18/501,832, filed Nov. 3, 2023.

Invitation To Pay Additional Fees And, Where Applicable, Protest Fee for International Application No. PCT/US2023/078706, dated Feb. 20, 2024. (13 pages).

* cited by examiner

STENT WITH ANTI-MIGRATION FEATURES

CROSS REFERENCE TO RELATED APPLICATIONS

This application claims the benefit of and priority to U.S. Provisional Patent Application Ser. No. 63/422,519, filed on Nov. 4, 2022, the disclosure of which is incorporated herein by reference.

TECHNICAL FIELD

The present disclosure pertains to medical devices, methods for manufacturing medical devices, and uses thereof. More particularly, the present disclosure pertains to a stent for implantation in a body lumen or for transluminal implantation, and associated methods.

BACKGROUND

A wide variety of intracorporeal medical devices have been developed for medical use, for example, surgical and/or intravascular use. In some cases, physicians have been able to use a stent to create a temporary opening between the gallbladder and the gastrointestinal (GI) tract to allow for drainage of fluid from the gallbladder in the case of a duct blockage. Without this technology, the other solution includes laparoscopic or percutaneous removal of the gallbladder which are high risk for the elderly, critically ill, and patients with co-morbidities. Of the known stents, endoluminal implants, and/or transluminal implants, there is an ongoing need to provide alternative configurations of stents, endoluminal implants, and/or transluminal implants.

SUMMARY

This disclosure provides design, material, manufacturing method, and use alternatives for medical devices. An example medical device may include a stent.

In a first example, a stent may comprise an elongated tubular body having a scaffolding forming a plurality of cells and a coating disposed over an outer surface of the elongated tubular body. The coating may comprise a first micro-porous layer and a macro-porous layer disposed over the micro-porous layer.

Alternatively or additionally to any of the examples above, in another example, the macro-porous layer may include a columnar structure.

Alternatively or additionally to any of the examples above, in another example, the macro-porous layer may include a plurality of loops.

Alternatively or additionally to any of the examples above, in another example, the plurality of loops may be stacked one on top of another to form a plurality of pillars.

Alternatively or additionally to any of the examples above, in another example, the plurality of pillars may extend radially from an outer surface of the micro-porous layer.

Alternatively or additionally to any of the examples above, in another example, at least some of the plurality of pillars may have a longitudinal axis extending at an oblique angle to a longitudinal axis of the elongated tubular body.

Alternatively or additionally to any of the examples above, in another example, at least some of the plurality of pillars may extend at an acute angle relative to the longitudinal axis that is between 0° and 90° and at least some of the plurality of pillars may extend at an obtuse angle relative to the longitudinal axis that is between 90° and 180°.

Alternatively or additionally to any of the examples above, in another example, at least some of the plurality of pillars may have a free end that is oriented towards a longitudinally centrally located pillar.

Alternatively or additionally to any of the examples above, in another example, a density of the plurality of pillars may increase towards a longitudinally centrally located pillar.

Alternatively or additionally to any of the examples above, in another example, a loop of the plurality of loops may be at least partially laterally spaced from a preceding loop.

Alternatively or additionally to any of the examples above, in another example, the stent may further comprise a second micro-porous layer disposed over the macro-porous layer.

In another example, a stent may comprise an elongated tubular body having a scaffolding forming a plurality of cells and a covering extending over the scaffolding to cover the plurality of cells of the scaffolding and a fabric sleeve disposed over at least a portion of the elongated tubular body. The fabric sleeve may be fabricated from one or more interwoven filaments defining a plurality of open cells.

Alternatively or additionally to any of the examples above, in another example, an entire length of the fabric sleeve may be positioned between a first flange proximate a first end of the elongate tubular body and a second flanged proximal a second end of the elongate tubular body.

Alternatively or additionally to any of the examples above, in another example, the fabric sleeve may be removably disposed over the elongated tubular body.

Alternatively or additionally to any of the examples above, in another example, the fabric sleeve may be formed from a bio-absorbable textile material.

Alternatively or additionally to any of the examples above, in another example, the fabric sleeve may be formed from a synthetic textile material.

In another example, a stent may comprise an elongated tubular body having a scaffolding forming a plurality of cells, a first polymer matrix disposed over the elongated tubular body, the first polymer matrix comprising a first plurality of fibers defining a plurality of pores and having a first density of the first plurality of fibers, and a second polymer matrix disposed over the elongated tubular body, the second polymer matrix comprising a second plurality of fibers defining a plurality of pores and having a second density of the second plurality of fibers. The second density of fibers may be less than the first density of fibers.

Alternatively or additionally to any of the examples above, in another example, the first polymer matrix may be configured to preclude tissue ingrowth.

Alternatively or additionally to any of the examples above, in another example, the second polymer matrix may be configured to encourage tissue ingrowth.

Alternatively or additionally to any of the examples above, in another example, the first plurality of fibers and the second plurality of fibers may be electro-spun.

Alternatively or additionally to any of the examples above, in another example, the stent may further comprise a bio-adhesive coating disposed over the second polymer matrix.

Alternatively or additionally to any of the examples above, in another example, a diameter of the first plurality of fibers may be less than a diameter of the second plurality of fibers.

In another example, a stent may comprise an elongated tubular body having a scaffolding forming a plurality of cells, a first polymer matrix disposed over the elongated tubular body, the first polymer matrix comprising a first plurality of fibers defining a plurality of pores and having a first density of the first plurality of fibers, and a hydrogel adhesive layer disposed over the first polymer matrix.

Alternatively or additionally to any of the examples above, in another example, the hydrogel advice layer may comprise gelatin, gelatin methacryloyl (GelMA), polyethylene glycol (PEG) based bio-adhesives, or chitosan.

In another example, a stent may comprise an elongated tubular body having a scaffolding forming a plurality of cells, a first polymer matrix disposed over the elongated tubular body, the first polymer matrix comprising a first plurality of fibers defining a plurality of pores and having a first density of the first plurality of fibers, and a hemostatic agent layer disposed over the first polymer matrix.

Alternatively or additionally to any of the examples above, in another example, the hemostatic agent layer may comprise kaolin and sodium montmorillonite.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
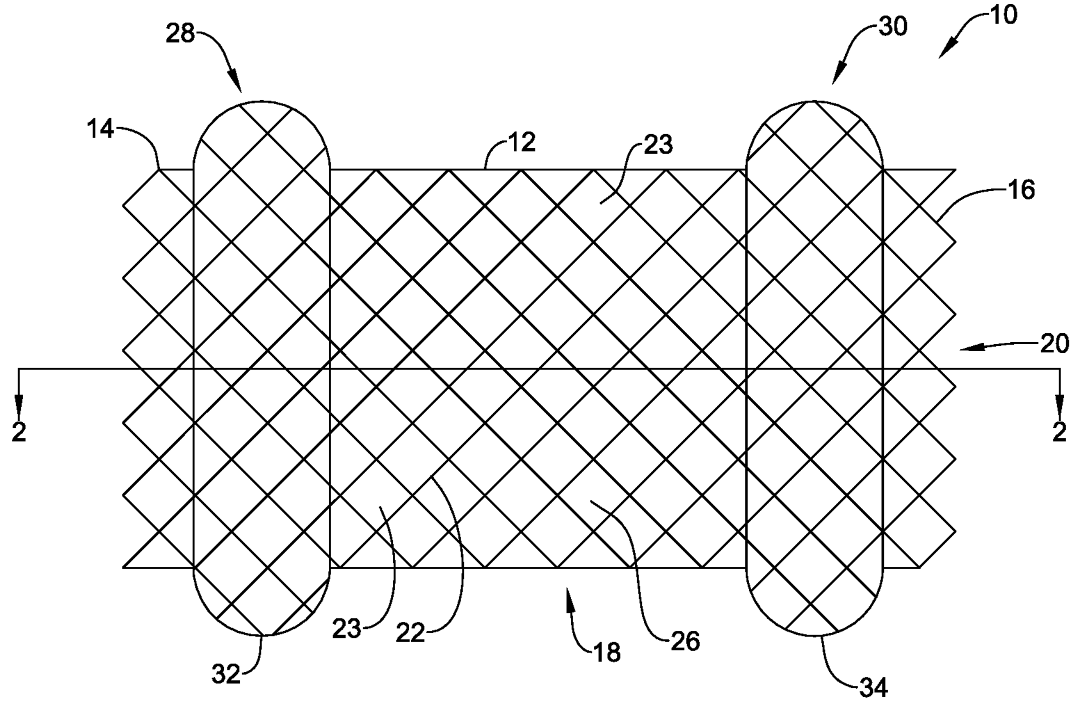
FIG. 1 is a side view of an illustrative stent.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

All numeric values are herein assumed to be modified by the term “about”, whether or not explicitly indicated. The term “about” generally refers to a range of numbers that one of skill in the art would consider equivalent to the recited value (i.e., having the same function or result). In many instances, the term “about” may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

In some cases, physicians have been able use a stent or transluminal implant to create an anastomosis or a temporary opening between the gallbladder and the gastrointestinal (GI) tract to allow for drainage of fluid from the gallbladder in the case of a duct blockage. Without this technology, the other solution includes laparoscopic or percutaneous removal of the gallbladder which are high risk for the elderly, critically ill, and patients with co-morbidities. Although this technology has helped make large advances in patient care, there are still challenges associated with transluminal drainage. For example, placing a stent between two non-adherent structures (e.g., a gastrojejunostomy, a hepaticogastrostomy, or a gallbladder drainage into either the stomach or duodenum, etc.) to form an anastomosis is technically challenging due to the lack of tools to visualize, stabilize, and, in some cases, inflate the target site. These challenging situations can lead to the stent failing to produce a hold between the two non-adherent structures/tissues. All of these challenges can lead to a failed procedure with serious complications. What may be desirable is a device and associated methods which make the post-procedure process easier on the patient as well as reduce long-term complications. While the present disclosure is discussed with respect to transluminal implants for forming an anastomosis, it should be understood that the devices described herein may be endoluminal implants as well. Further, the implant location is not limited to a particular anatomical location.

Figure 2:
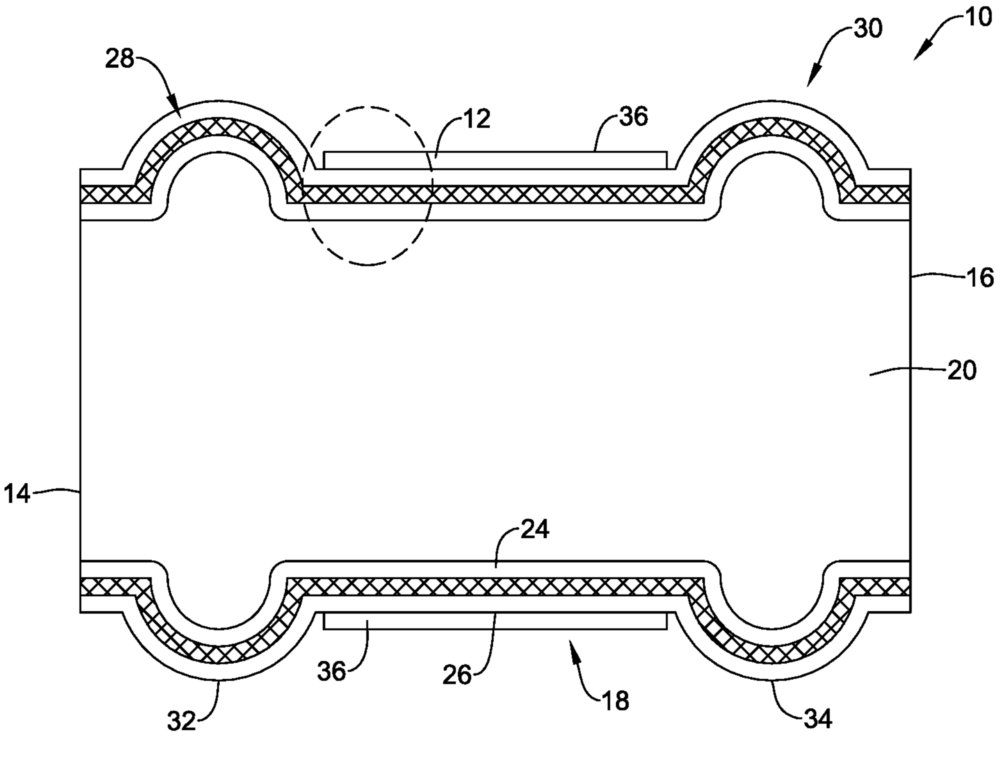
FIG. 2 is a cross-sectional view of the illustrative stent of FIG. 1.
Figure 3:
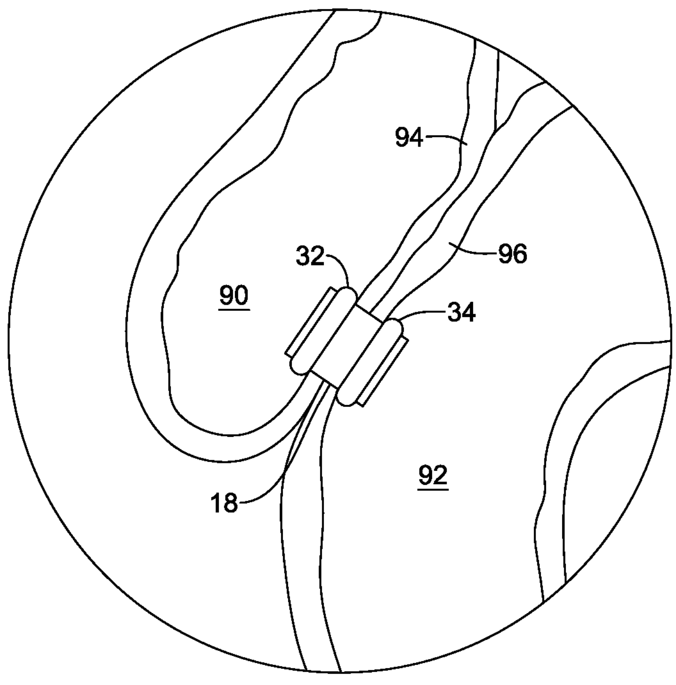
FIG. 3 is a schematic view of the illustrative stent of FIG. 1 implanted in a body.

FIG. 1 illustrates a side view of an illustrative implant 10, such as, but not limited to, a stent. FIG. 2 illustrates a cross-sectional view of the illustrative stent 10, taken at line 2-2 of FIG. 1. FIG. 3 illustrates a schematic view of the illustrative stent 10 implanted in the body of a patient to form an anastomosis. In some instances, the stent 10 may be formed from an elongated tubular member 12. While the stent 10 is described as generally tubular, it is contemplated that the stent 10 may take any cross-sectional shape desired. The stent 10 may have a first, or proximal, end 14, a second, or distal, end 16, and an intermediate region 18 disposed between the first end 14 and the second end 16. The stent 10 may include a lumen 20 extending from a first opening adjacent the first end 14 to a second opening adjacent to the second end 16 to allow for the passage fluids, etc. therethrough.

The stent 10 may be radially expandable from a first radially collapsed configuration (not explicitly shown) to a second radially expanded configuration, as shown in FIGS. 1-3. The stent 10 may be structured to extend across two non-adherent structures/tissues and to apply a radially outward pressure to create an opening or passage between the two non-adherent structures/tissues, thereby forming an anastomosis between the two separate anatomical structures.

The tubular member 12 of the stent 10 may have a scaffold structure, fabricated from one or more, or a plurality of interwoven filaments or struts 22. The scaffold structure may extend from the first end 14 to the second end 16 of the stent 10. For example, the scaffold structure, and thus the filament(s) thereof, may extend continuously from the first end 14 to the second end 16 of the stent 10. In some embodiments, the stent 10 may be formed with one filament interwoven with itself (e.g., knitted) to form the scaffold structure. In other embodiments, the stent 10 may be formed with several interwoven filaments (e.g., braided) to form the scaffold structure. Thus, in such instances one or more of the filament(s) forming the scaffold structure may extend continuously from the first end 14 to the second end 16 of the stent 10. In still another embodiment, the stent 10 may include a laser cut tubular member to form the scaffold structure. A laser cut tubular member may have an open and/or closed cell geometry including one or more interconnected struts formed as a monolithic structure from the tubular member. In such instances, the laser cut tubular member forming the scaffold structure may extend continuously from the first end 14 to the second end 16 of the stent 10.

Figure 4:
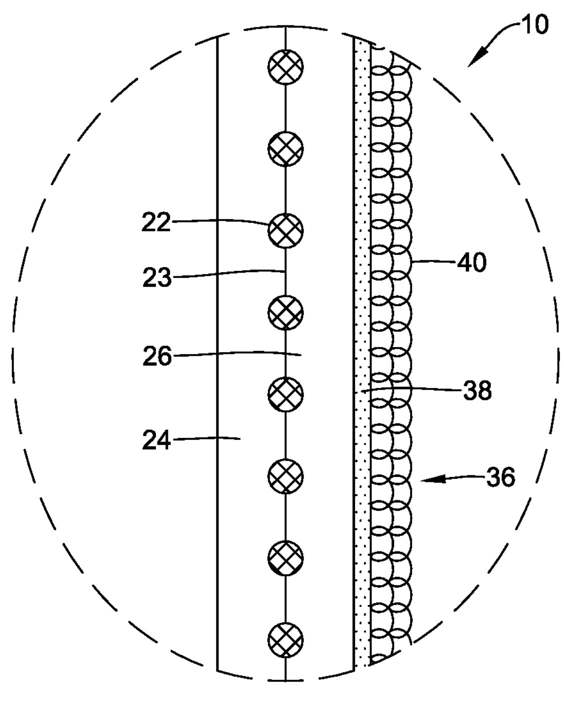
FIG. 4 is an enlarged cross-sectional view of a portion of the illustrative stent of FIG. 2.

In some instances, an inner and/or outer surface of the scaffold structure of the stent may be entirely, substantially or partially, covered with a polymeric covering or layer 24, 26 (see, for example, FIG. 2). For example, a covering or coating may extend across the open cells of the scaffold structure to prevent tissue ingrowth into the lumen of the stent 10. However, in some embodiments one or both of the polymeric coverings 24, 26 may be omitted. For example, in some embodiments the stent 10 may include only the outer polymeric covering 26 on an outer surface of the scaffold structure. In other embodiments the stent 10 may include only the inner polymeric covering 24 on an inner surface of the scaffold structure. In some instances, the inner layer 24 and the outer layer 26 may be formed as a unitary structure. In other embodiments, the inner layer 24 and the outer layer 26 may be formed as separate layers. The inner and outer layers 24, 26 may be formed from the same material or different materials, as desired. The inner 24 and/or outer layer 26 may span or be disposed within openings or interstices defined between adjacent stent filaments or struts 22 of the scaffold structure, as more clearly shown in FIG. 4 which illustrates an enlarged view of a portion of the stent 10 shown in dashed lines in FIG. 2. It can be appreciated that as inner layer 24 and outer layer 26 extend outwardly and inwardly, respectively, they may touch and/or form an interface region within the spaces (e.g., openings, cells, interstices) 23 in the wall of the scaffold structure of the stent 10. For example, the detailed view of FIG. 4 shows that both the inner and outer layers 24, 26 may extend into the openings 23 defined between adjacent stent struts 22 and form an interface region. Further, the inner and outer layers 24, 26 may additionally extend between adjacent filaments or struts 22, thereby filling any space between adjacent filaments or strut members 22, and thus prevent tissue ingrowth into the lumen of the stent 10.

It is contemplated that the scaffold structure, e.g., the filaments and/or struts, of the stent 10 can be made from a number of different materials such as, but not limited to, metals, metal alloys, shape memory alloys, and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, nitinol and Elgiloy®. Depending on the material selected for construction, the stent 10 may be self-expanding or require an external force to radially expand the stent 10. In some embodiments, filaments may be used to make the stent 10, which may be composite filaments, for example, having an outer shell made of nitinol and having a platinum core. It is further contemplated the filaments of the stent 10 may be formed from polymers including, but not limited to, polyethylene terephthalate (PET).

In some instances, in the radially expanded configuration, the stent 10 may include a first end region 28 proximate to the first end 14 and a second end region 30 proximate to the second end 16. In some embodiments, the first end region 28 and the second end region 30 may include shoulders or enlarged regions, such as flanges 32, 34 positioned adjacent to the first end 14 and the second end 16 of the stent 10. The flanges 32, 34 may be configured to engage an interior portion of the walls of the body cavity or body lumen. For example, the first flange 32 may be positioned against an interior of a first body lumen and the second flange 34 may be positioned against an interior of a second body lumen different from the first body lumen. Thus, the stent 10 may be positioned to traverse between two separate anatomical structures. For example, referring to FIG. 3, the stent 10 is positioned such that it extends between the gallbladder 90 and the duodenum 92. The first flange 32 may be positioned in the gallbladder 90 and the second flange 34 may be positioned in the duodenum 92. The intermediate region or body 18 of the stent 10 extending between the first flange 32 and the second flange 34 may extend through the wall 94 of the gallbladder 90 and the wall 96 of the duodenum 92. In some cases, the first flange 32 may contact an interior of the wall 94 of the gallbladder 90 and/or the second flange 34 may contact an interior of the wall 96 of the duodenum. However, this is not required.

In some embodiments, the flanges 32, 34 may have a larger diameter than the intermediate region or body 18 of the stent 10 located between the end regions 28, 30 to prevent or help prevent the stent 10 from migrating once placed within a body cavity, body lumen, or across body cavities or lumens. It is contemplated that the transition from the cross-sectional area of the intermediate region or body 18 to the retention features or flanges 32, 34 may be gradual, sloped, or occur in an abrupt step-wise manner, as desired. In some cases, the flanges 32, 34 may have a curved semi-hemispherical shape that gradually increases in cross-sectional dimensions and then gradually decreases in cross-sectional dimension in a direction such that the first and/or second ends 14, 16 have a similar cross-sectional dimension to the intermediate region or body 18. However, this is not required. Other shapes and/or configurations may be used, as desired.

In some embodiments, the first flange 32 may have a first outer diameter and the second flange 34 may have a second outer diameter. The outer diameter of the first flange 32 and/or the second flange 34 may be greater than the outer diameter of the intermediate region or body 18. In some instances, the first and second outer diameters may be approximately the same, while in other instances, the first and second outer diameters may be different. In some embodiments, the stent 10 may include only one flange 32, 34, or the stent 10 may not include a flange, if desired. For example, the first end region 28 may include a flange 32 while the second end region 30 may have an outer diameter similar to that of the intermediate region or body 18. It is further contemplated that the second end region 30 may include a flange 34 while the first end region 28 may have an outer diameter similar to that of an outer diameter of the intermediate region or body 18. In some embodiments, the stent 10 may have a uniform outer diameter from the first end 14 to the second end 16. In some embodiments, the outer diameter of the intermediate region or body 18 may be in the range of 15 to 25 millimeters. The outer diameter of the flanges 32, 34 may be in the range of 20 to 30 millimeters. It is contemplated that the outer diameter of the stent 10 may be varied to suit the desired application.

As can be seen more clearly in FIG. 4, in some embodiments, an outer surface of the stent 10 may include a coating 36 configured to encourage ingrowth of the tissue post-procedure and/or post-implantation of the stent 10. The coating 36 may be deposited on at least a portion of the outer covering 26, or on at least a portion of the inner covering 24 in instances in which the outer covering 26 is absent. In the absence of the inner and/or the outer covering 24, 26, the coating 36 may be disposed on the struts 22 and/or within at least portion of the plurality of openings 23. In some cases, the coating 36 may be configured to induce ingrowth of new tissue around and through the stent 10. Referring briefly to the example of FIG. 3, the coating 36 may be configured to induce tissue growth which causes the opening formed through the walls 94, 96 of the cavities 90, 92 to become a natural part of the body. For example, in this situation, the orifice would remain open to permanently drain the gallbladder with or without the stent 10 in place. The stent 10 may be placed in the desired treatment location and left in place until tissue ingrowth has formed a natural orifice or pathway between two non-adherent tissues/structures. It is contemplated that the ingrowth of new healthy tissue around the stent 10 may reduce the likelihood of stent migration as the healthy tissue may grip onto the stent 10 and the natural peristalsis of the body would not be enough to dislodge the stent 10 from the ingrown tissue. However, in some instances the stent 10 may still be removed through endoscopic means after several weeks, if needed, leaving a conduit of newly formed tissue spanning the two non-adherent tissues/structures to form an anastomosis therebetween.

Returning to FIG. 4, the coating 36 may include a first or inner micro-porous layer 38 and a second or outer macro-porous layer 40 positioned over the inner micro-porous layer 38. While not explicitly shown, in some cases, a second micro-porous layer may be deposited over the macro-porous layer 40. Generally, the inner micro-porous layer 38 may improve cellular adhesion to the surface of the stent 10 to limit stent migration while the macro-porous layer 40 may encourage vascular structures to grow along the surface of the stent 10 surface to encourage anastomosis formation. For example, the inner micro-porous layer 38 may encourage cell attachment while the outer macro-porous layer 40 may encourage tissue ingrowth. It is further contemplated that the coating 36 may inhibit or limit a foreign body response. Inclusion of both the inner micro-porous layer 38 and the macro-porous layer 40 may encourage an anastomosis to grow from natural tissue between the gallbladder 90 and the stomach/duodenum 92 (or two other non-adherent structures/tissues) without the stent 10 migrating out of position. In some instances, the inner micro-porous layer 38 and/or the outer macro-porous layer 40 may be absorbed into the body tissue over time as the new tissue in-growth occurs. As the tissue from the two non-adherent structures grows, the tissues from each of the non-adherent structures may grow together or connect to form a tissue conduit between the non-adherent structures. This may allow a formed tissue anastomosis to remain in the body even after the stent 10 (with the inner and outer layers 24, 26) is removed.

The coating 36 may be formed through any desired process. For instance, the coating 36 may be formed through a combination of spray coating and direct-ink-writing (DIW). For example, the inner micro-porous layer 38 may be created by spraying the stent 10 with a sprayable ink. As used herein, "ink" may be a liquid used for the printing of the inner micro-porous layer 38 on the stent 10. The ink may be sprayed in liquid form and any solvents evaporated leaving behind solids having a micropatterned texture. In some cases, the inner micro-porous layer 38 may need to be cured to solidify the coating. The inner micro-porous layer 38 may have interconnected pores in the range of 2 micrometers (μm) or less, or in the range of about 0.05 μm to about 2 μm. The inner micro-porous layer 38 may have a thickness in the micrometer range. For example, the inner micro-porous layer 38 may have a thickness in the range of about 10 μm to about 80 μm, about 20 μm to about 60 μm, or about μm. In some cases, the sprayable ink may be a sprayable silicone ink. It is contemplated that the sprayable ink may include additives configured to increase porosity by removing the additives after curing the sprayable ink.

The macro-porous layer 40 may be formed by extruding a high viscosity material over the stent 10 using, for example, 3-D printing to form a columnar structure extending above the micro-porous layer 38. In some instances, the columnar structure may include a plurality of columns extending from the micro-porous layer 38 with spaces therebetween. In some instances, the columnar structure forming the macro-porous layer may be considered a rope-coil layer. The rope-coil layer gets its name from the tendency of the material to coil like a rope as it is expelled from the extruder. It is contemplated that the material may have a viscosity which allows the material to retain the cross-sectional dimension of the extruder as it is applied to the stent 10. For example, the material may be resistant to flow during extrusion and/or after extrusion. It is contemplated that the material may be any biocompatible or bioabsorbable material, as desired. The thickness of the macro-porous layer 40 may have a thickness (measured in a direction extending outward from the outer surface of the micro-porous layer 38) in a range from at least 1 micron (μm) to at least one millimeter (mm), such as, e.g., from about 1.5 μm to about 850 μm, from about 5 μm to about 10 μm, from about 50 μm to about 250 μm, from about 350 μm to about 750 μm, from about 450 μm to about 600 μm, from about 650 μm to about 950 μm, or about 300 μm to about 550 μm. The pattern of the macro-porous layer 40 may be determined, at least in part, by a speed of movement of the stent 10 (e.g., axial movement relative to the extruder), the flow rate of the material from the extruder, the diameter of the extruder, and/or the distance between the extruder and the stent 10. For example, if the stent 10 is moved relative to the extruder, the material may form a plurality of loops whereas if the stent 10 is stationary, the loops may coil on top of one another to form a vertically rising coil (e.g., resembling a spring).

Figure 5:
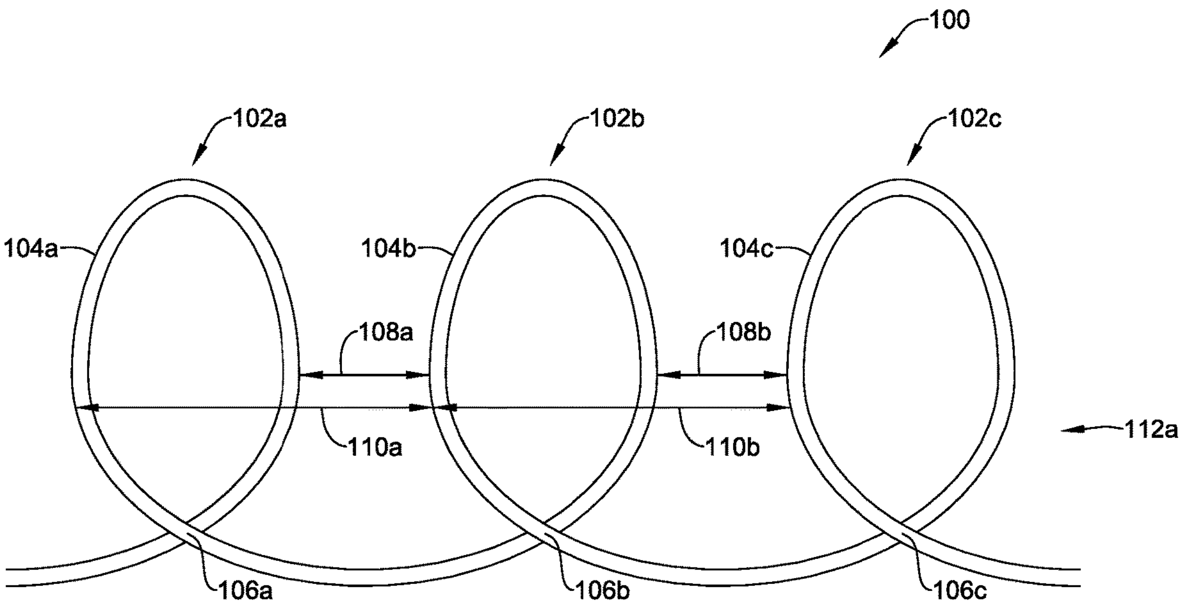
FIG. 5 is a schematic view of an illustrative pattern of a macro-porous layer.

FIG. 5 illustrates a schematic view of an illustrative pattern 100 of the macro-porous layer 40 when the stent 10 is moved relative to the extruder. The macro-porous layer 40 may be formed as one or more rows 112 of a plurality of loops 102*a*, 102*b*, 102*c* (collectively, 102). The loops 102 may each include a loop portion 104*a*, 104*b*, 104*c* (collectively, 104) and an overlapping base portion 106*a*, 106*b*, 106*c* (collectively, 106). The overlapping base portion 106*a*, 106*b*, 106*c* is understood as the portion of the loops 102 in which one segment of the filament overlaps or crosses over a second segment of the filament, with the segment of the filament forming the loop portion 104*a*, 104*b*, 104*c* extending therebetween. In the illustrated pattern 100, there is a gap 108*a*, 108*b* between adjacent loop portions 104 such that a subsequent loop 102*b*, 102*c* is free from contact with the preceding loop 102*a*, 102*b*. However, this is not required. The pattern 100 may be formed such that adjacent loops 102 overlap each other. The amount of overlap can range from the loops 102 formed one on top of another to adjacent loop portions 104 just contacting one another. For example, the distance 110*a*, 110*b* (collectively, 110) between like positions on adjacent loops 102 may be zero or substantially zero such that the loops 102 are vertically stacked on one another. In other cases, the distance 110 between like positions on adjacent loops 102 may be less than a width of a loop 102 such than a subsequent loop is partially formed over the preceding loop 102. It is further contemplated that laterally adjacent loops 102 may be free from connection with one another. For example, in some cases, loops 102 may form a first vertically extending column of stacked loops 102, as will be described in more detail herein.

Figure 6:
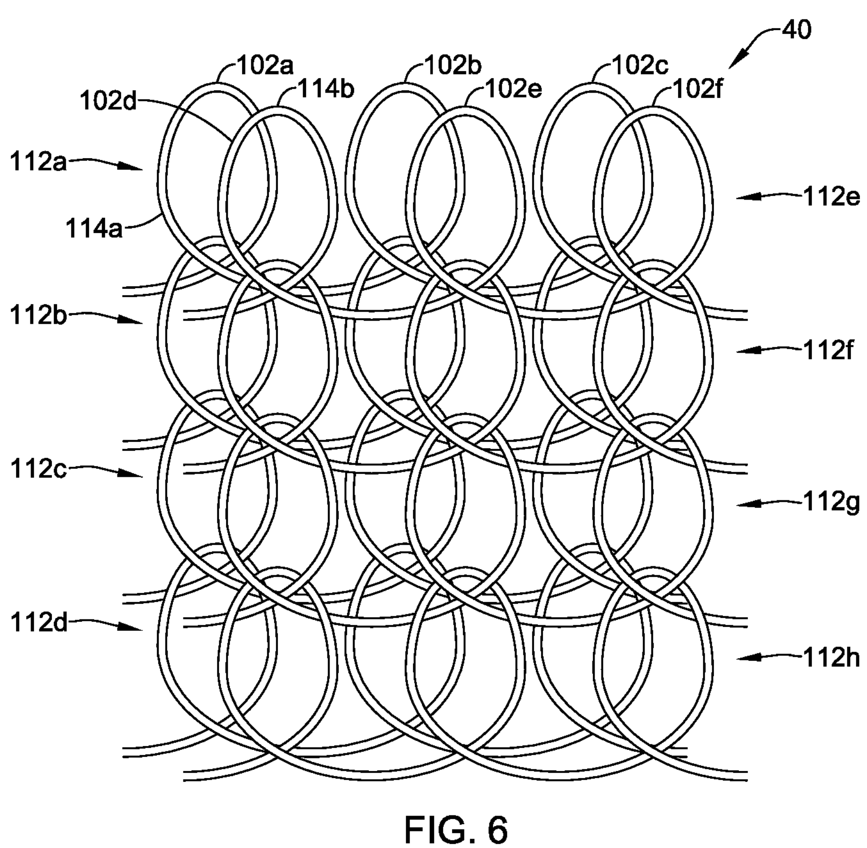
FIG. 6 is a schematic top view of an illustrative macro-porous layer.

FIG. 6 which illustrates an enlarged top view of a portion of the macro-porous layer 40. The macro-porous layer 40 may include a plurality of layers 114*a*, 114*b* (collectively, 114) each having a plurality of rows 112*a-h* formed from a plurality of loops 102*a-f*, where not all loops have been formally identified with a reference numeral for brevity and ease of understanding. The innermost layer 114*a* may be applied to the outer surface of the stent 10 (e.g., over the inner micro-porous layer 38) and then an outer layer 114*b* positioned over the inner layer 114*a*. In some cases, the inner micro-porous layer 38 and the macro-porous layer may be applied and adhered directly to an outer surface (e.g., outer layer 26, if so provided) while in other cases, the inner micro-porous layer 38 and the macro-porous layer may be applied to a sleeve which is positioned over but not necessarily coupled to the outer surface of the stent 10. While FIG. 6 illustrates two layers 114, it is contemplated that the macro-porous layer 40 may include fewer than two or more than two layers, as desired.

The first layer 114*a* may be formed by rotating the stent 10 about its longitudinal axis (relative to the extruder) as the material is extruded to form a circumferentially extending row 112*a*. The stent 10 may then be axially displaced and another circumferentially extending row 112*b* deposited. This may be repeated for as many rows as desired. In another example, the first layer 114*a* may be formed by axially displacing the stent 10 (relative to the extruder) as the material is extruded to form a longitudinally extending row. The stent 10 may then be rotated about the longitudinal axis and another longitudinally extending row deposited. This may be repeated for as many rows as desired.

Once the first layer 114*a* is complete, one or more additional layers 114*b* may be deposited over the preceding layer. In the illustrated embodiment of FIG. 6, the second layer 114*b* is shown such that the rows 112*e-h* are vertically and horizontally offset from the rows 112*a-d* of the first layer 114*a*. However, this is not required. In some cases, the second layer 114*b* may be applied such that the rows 112*e-h* (and corresponding loops 102*d-f*) align with or are stacked upon the rows 112*a-d* (and corresponding loops 102*a-c*) of the preceding layer 114*a*. In other examples, the second layer 114*b* may be applied at an angle relative to the first layer 114*a*. For example, the rows 112*e-h* of the second layer 114*b* may be non-parallel to the rows 112*a-d* of the first layer 114*a*. In other examples, the rows 112*e-h* of the second layer 114*b* may be vertically or horizontally offset from the rows 112*a-d* of the first layer 114*a*.

The inner micro-porous layer 38 and/or the macro-porous layer 40 may be deposited over an entirety of an outer surface of the stent 10 or less than an entirety, as desired. For example, in some cases, the inner micro-porous layer 38 and/or the macro-porous layer 40 may be deposited on the intermediate region or body 18 of the stent 10 extending between the flanges 32, 34, as shown in FIG. 2, while the flanges 32, 34 may be devoid of the inner micro-porous layer 38 and/or the macro-porous layer 40. However, it should be understood that the inner micro-porous layer 38 and/or the macro-porous layer 40 may be deposited in any configuration desired including uniform patterns, eccentric arrangements, less than an entire circumference of the stent 10, less than an entire length of the stent 10, combinations thereof, etc. For example, the inner micro-porous layer 38 and/or the macro-porous layer 40 may be selectively deposited over the stent 10 to control fixation characteristics of the stent to a target treatment site.

In some examples, the surface of the stent 10 may be mapped or scanned prior depositing the inner micro-porous layer 38 and/or the macro-porous layer 40. This may allow the control panel of the extruder to understand the topography of the surface and to apply the coating 36 to a desired height. For example, the extruder may be configured to apply the coating 36 in a manner which allows the outer surface to have a uniform outer dimension regardless of any variations in cross-sectional dimension of the base material (e.g., the scaffold structure of the stent 10).

Figure 7A:
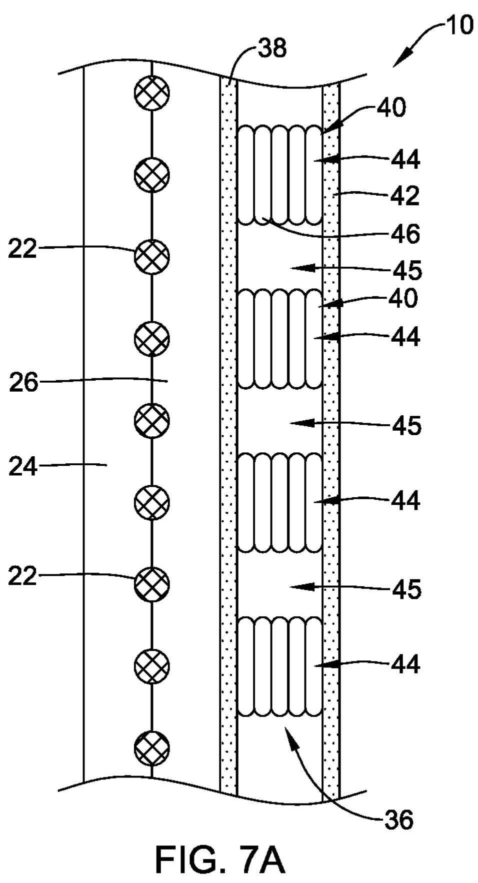
FIG. 7A is a partial cross-section of the stent of FIG. 1 having an alternative macro-porous layer with an alternative columnar structure and outer micro-porous layer.

FIG. 7A is a partial cross-section of the stent 10 having an alternative macro-porous layer 40' with an alternative loop arrangement. The coating 36 may include a first or inner micro-porous layer 38 and a second or intermediate macro-porous layer 40' positioned over or exterior of the inner micro-porous layer 38, and a and a third or outer micro-porous layer 42 positioned over or exterior of the macro-porous layer 40'. The macro-porous layer 40' may include a columnar structure, such as a plurality of pillars 44. Each pillar 44 may be formed from a plurality of coiled loops 46 stacked on top of the other like a coil of rope or a spring and extend radially outwards from the micro-porous layer 38. While the pillars 44 are illustrated as each having five loops 46, each pillar 44 may have fewer than five or more than five loops 46, as desired, to achieve a desired height. It is further contemplated that the pillars 44 may have varying numbers of loops 46 to create pillars 44 having different heights. The pillars 44 may be axially and/or circumferentially spaced from one another in any arrangement desired. In some examples, two or more of the pillars 44 may be in contact with one another.

The outer micro-porous layer 42 may be created by spraying the stent 10 with a sprayable ink after the macro-porous layer 40' has been deposited. The ink may be sprayed in liquid form and any solvents evaporated leaving behind solids having a micropatterned texture. In some cases, the outer micro-porous layer 42 may need to be cured to solidify the coating. The outer micro-porous layer 42 may have interconnected pores in the range of 2 micrometers (μm) or less, or in the range of about 0.05 (μm) to about 2 μm. The outer micro-porous layer 42 may have a thickness in the micrometer range. For example, the outer micro-porous layer 42 may have a thickness in the range of about 10 μm to about 80 μm, about 20 μm to about 60 μm, or about 40 μm. In some cases, the sprayable ink may be a sprayable silicone ink. It is contemplated that the sprayable ink may include additives configured to be increase porosity by removing the additives after curing the sprayable ink.

In some embodiments, the outer micro-porous layer 42 may be formulated to provide additional nutrients to further encourage cellular ingrowth. For example, the outer micro-porous layer 42 may include or be derived from nutrient solutions such as, but not limited to, nutrient agar or nutrient broth. Alternatively, or additionally, a coating including or derived from nutrient solutions may be sprayed or otherwise deposited over the outer micro-porous layer 42 (or over the macro-porous layer 40, 40' in the absence of an outer micro-porous layer 42). Nutrient solutions may be commonly used in tissue cultures to encourage tissue growth in micropropagation cultures and could be used to similarly encourage tissue growth in the body post-procedure. This added spray/coating may last for a predetermined length of time such as several days or several weeks, after which point the stent 10 may be removed, if applicable, and the body would have naturally formed an anastomosis with natural tissue growing between and connecting the gallbladder and duodenum or stomach (or two other non-adherent tissues/structures).

The inner micro-porous layer 38, the macro-porous layer 40', and/or the outer micro-porous layer 42 may be deposited over an entirety of an outer surface of the stent 10 or less than an entirety, as desired. For example, in some cases, the inner micro-porous layer 38, the macro-porous layer 40', and/or the outer micro-porous layer 42 may be deposited on the intermediate region or body 18 of the stent 10 extending between the flanges 32, 34, while the flanges 32, 34 may be devoid of the inner micro-porous layer 38, the macro-porous layer 40', and/or the outer micro-porous layer 42. However, it should be understood that the inner micro-porous layer 38, the outer micro-porous layer 42, and/or the macro-porous layer 40 may be deposited in any configuration desired including uniform patterns, eccentric arrangements, less than an entire circumference of the stent 10, less than an entire length of the stent 10, combinations thereof, etc.

As shown in FIG. 7A, the outer micro-porous layer 42 may extend over the columnar structure formed by the plurality of pillars 44 and span the spaces been adjacent pillars 44. By spanning over the spaces between adjacent pillars 44, voids 45 may be defined between the outer surface of the inner micro-porous layer 38 and the outer micro-porous layer 42, between adjacent pillars 44. The voids 45 may permit tissue ingrowth therein subsequent to implantation which may facilitate formation of a tissue conduit to form anastomosis between two anatomical structures.

Figure 7B:
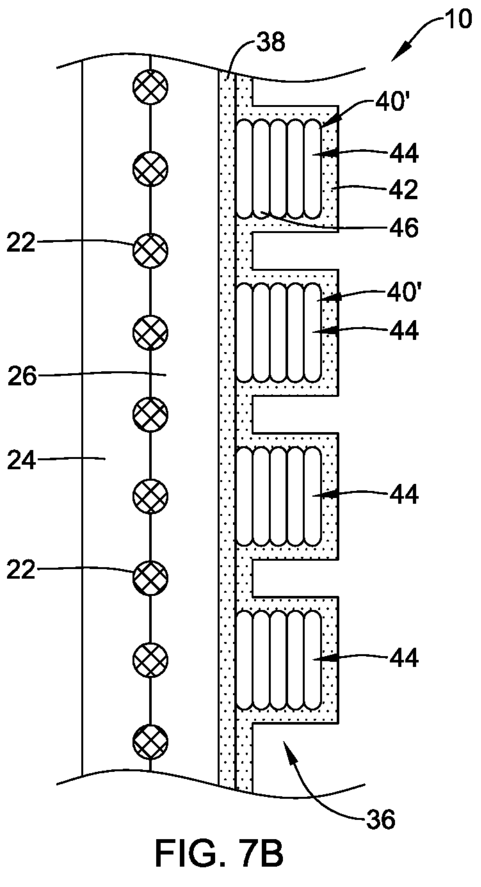
FIG. 7B is a partial cross-section of the stent of FIG. 1 having an alternative macro-porous layer and outer micro-porous layer.

In an alternative configuration, shown in FIG. 7B, the outer micro-porous layer 42 may extend over the columnar structure formed by the plurality of pillars 44 and extend radially inward in the spaces between adjacent pillars 44 to contact the outer surface of the inner micro-porous layer 38 between adjacent pillars 44.

Figure 8A:
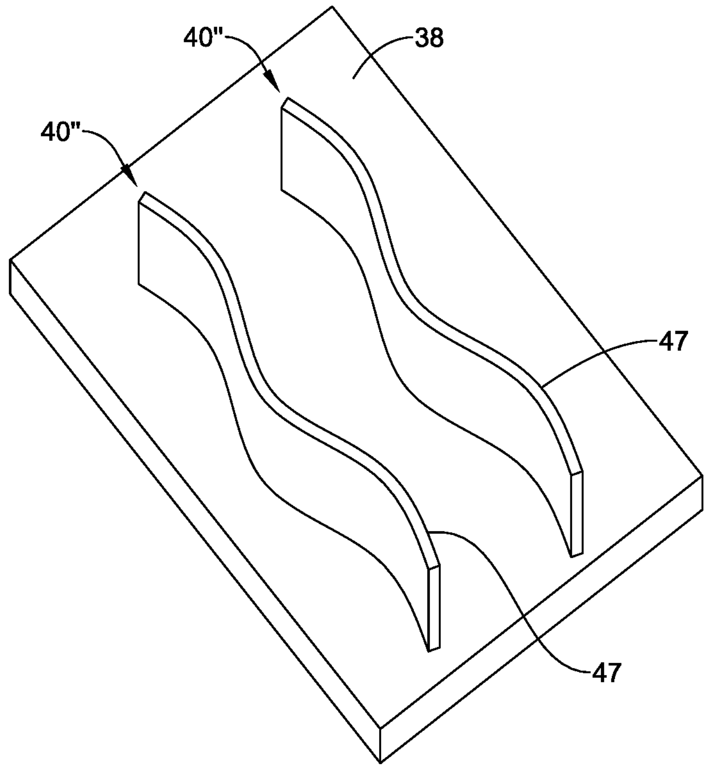
FIG. 8A is a partial perspective view of a portion of the stent of FIG. 1 having an alternative macro-porous layer.

FIG. 8A illustrates another configuration of a macro-porous layer 40" extending above the inner micro-porous layer 38. It is noted that the outer micro-porous layer 42 has been excluded from FIG. 8A for clarity, but could be provided over the macro-porous layer 40" as shown in FIG. 7A or FIG. 7B. The macro-porous layer 40" may include a columnar structure formed of a plurality of columns, such as elongated baffles or partitions 47. The baffles or partitions 47 may extend longitudinally, circumferentially, sinusoidally, or in another origination or arrangement. The baffle or partitions 47 may extend between the outer surface of the inner micro-porous layer 38 to the inner surface of the outer micro-porous layer 42, providing voids therebetween for tissue ingrowth. The baffles or partitions 47 may be formed similar to the pillars 44, discussed above, such as by multiple layers of a 3-D printing process.

Figure 8B:
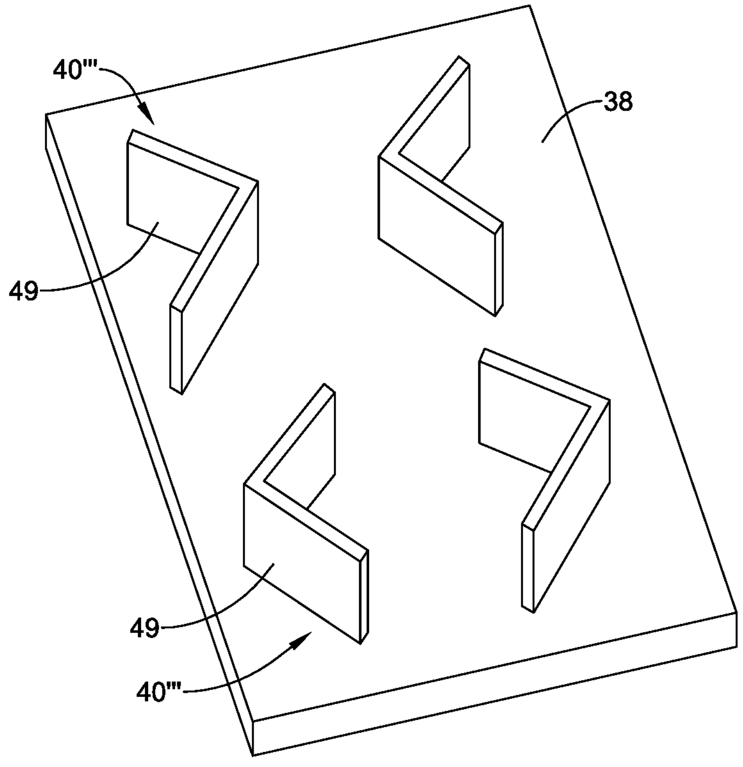
FIG. 8B is a partial perspective view of a portion of the stent of FIG. 1 having an alternative macro-porous layer.

FIG. 8B illustrates another configuration of a macro-porous layer 40''' extending above the inner micro-porous layer 38. It is noted that the outer micro-porous layer 42 has been excluded from FIG. 8B for clarity, but could be provided over the macro-porous layer 40' as shown in FIG. 7A or FIG. 7B. The macro-porous layer 40''' may include a columnar structure formed of a plurality of columns, such as walls or struts 49. The walls or struts 49 may extend in any desired origination or arrangement. The walls or struts 49 may extend between the outer surface of the inner micro-porous layer 38 to the inner surface of the outer micro-porous layer 42, providing voids therebetween for tissue ingrowth.

Figure 9A:
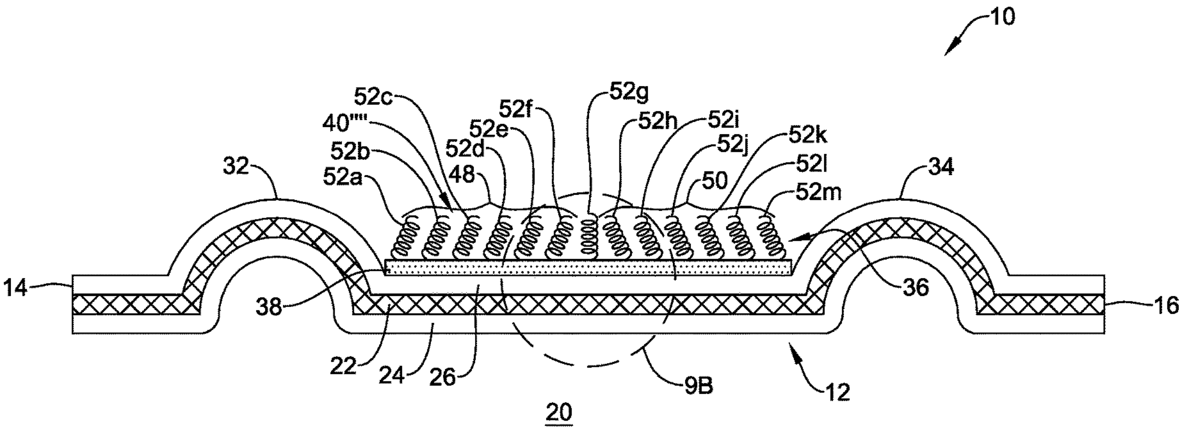
FIG. 9A is a partial schematic cross-sectional view of the illustrative stent of FIG. 1 depicting another illustrative arrangement of a plurality of pillars.

FIG. 9A illustrates a partial schematic cross-sectional view of the illustrative stent 10 depicting another illustrative arrangement of a columnar structure including a plurality of pillars 52*a-m* (collectively, 52) forming another illustrative macro-porous layer 40"". The pillars 52 may be similar in form and function to the pillars 44 described herein. In the illustrated embodiment, the pillars 52 may be deposited such that tissue growth from the two different non-adherent tissues/structures is towards one another (e.g., towards a central pillar 52*g*). For example, the macro-porous layer 40"" may include a first group 48 of pillars 52*a-f* extending from a location proximate the first flange 32 and towards a mid-point of the pillars 52 (e.g., towards the middle pillar 52*g*) at a medial point of the body 18 of the stent 10 and a second group 50 of pillars 52*h-m* extending from a location proximate the second flange 34 and towards a mid-point of the pillars 52 (e.g., towards the centrally located pillar 52*g*) at the medial point of the body 18 of the stent 10. While the middle pillar 52*g* is illustrated as centrally located along the length of the stent 10, this is not required. In some cases, the mid-point of the pillars 52 may not correspond to the mid-point of the stent 10, but may be at a different medial location along the body 18 of the stent 10. The first group 48 of pillars 52*a-f* may be oriented such that a longitudinal axis of the pillars 52*a-f* extends at a non-orthogonal angle (e.g., an oblique angle) relative to a longitudinal axis of the stent 10 such that a free end (e.g., radially spaced from the stent 10) of each of the pillars 52*a-f* points toward the centrally located pillar 52*g*. Similarly, the second group 50 of pillars 52*h-m* may also be oriented such that a longitudinal axis of the pillars 52*h-m* extends at a non-orthogonal angle (e.g., an oblique angle) relative to the longitudinal axis of the stent 10 such that a free end (e.g., radially spaced from the stent 10) of each of the pillars 52*h-m* points toward the centrally located pillar 52*g*. It is noted that the outer micro-porous layer 42 has been excluded from FIG. 9A for clarity, but could be provided over the macro-porous layer 40'''' as shown in FIG. 7A or FIG. 7B.

Figure 9B:
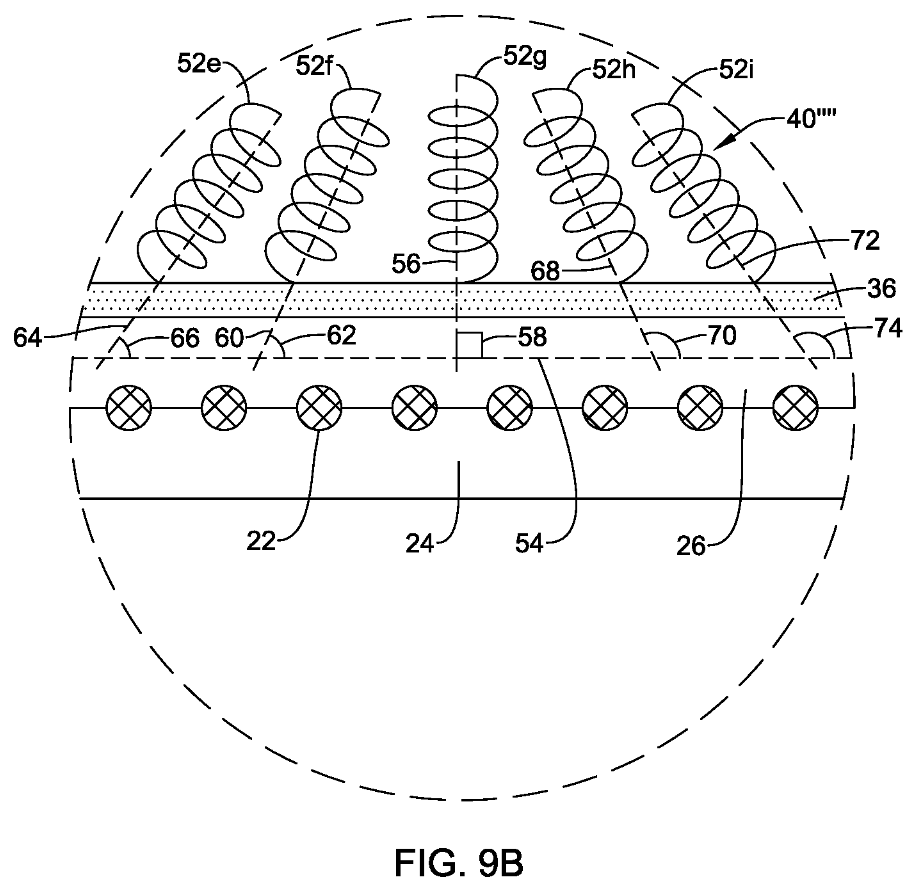
FIG. 9B is an enlarged view of a portion of the stent of FIG. 9A.

FIG. 9B illustrates an enlarged view of a portion of the stent 10 shown in dashed lines in FIG. 9A. The middle or centrally located pillar 52*g* may have a longitudinal axis 56 that is at a generally orthogonal angle 58 relative to the longitudinal axis 54 of the stent 10. The first group 48 of pillars 52*a-f* may extend at an oblique angle relative to the longitudinal axis that is between 0° and 90°. The angle of the first group 48 of pillars 52*a-f* may be uniform along the length of the stent 10, or the angle of the first group 48 of pillars 52*a-f* may become progressively greater towards the centrally located pillar 52*g*. For example, the first pillar 52*f* proximate the centrally located pillar 52*g* may have a longitudinal axis 60 that extends at a first non-orthogonal (e.g., acute) angle 62 relative to the longitudinal axis 54 of the stent 10 and the next second pillar 52*e* may also have a longitudinal axis 64 that extends at a second non-orthogonal (e.g., acute) angle 66 relative to the longitudinal axis 54. The first acute angle 62 may be less than 90° but greater than the second acute angle. Moving from the central located pillar 52*g* toward the first flange 32, each pillar 52*a-f* of the first group 48 may have an acute angle that is less than the acute angle of the pillar 52*a-f* immediately adjacent thereto. However, this is not required. In some cases, each of the pillars 52*a-f* of the first group 48 may have the same non-orthogonal (e.g., acute) angle. In yet other embodiments, the angle of the pillars 52*a-f* of the first group 48 may vary in an eccentric or non-uniform manner.

The second group 50 of pillars 52*h-m* may extend at an oblique angle relative to the longitudinal axis that is between 90° and 180°. The angle of the second group 50 of pillars 52*h-m* may be uniform along the length of the stent 10, or the angle of the second group 50 of pillars 52*h-m* may become progressively less towards the centrally located pillar 52*g*. For example, the first pillar 52*h* proximate the centrally located pillar 52*g* may have a longitudinal axis 68 that extends at a third non-orthogonal (e.g., obtuse) angle 70 relative to the longitudinal axis 54 of the stent 10 and the next second pillar 52*i* may also have a longitudinal axis 72 that extends at a fourth non-orthogonal (e.g., obtuse) angle 74 relative to the longitudinal axis 54. The third obtuse angle 70 may be greater than 90° but less than the fourth obtuse angle. Moving from the central located pillar 52*g* toward the second flange 34, each pillar 52*h-m* of the second group 50 may have an obtuse angle that is greater than the pillar 52*h-m* immediately adjacent thereto. However, this is not required. In some cases, each of the pillars 52*h-m* of the second group 50 may have the same non-orthogonal (e.g., obtuse) angle. In yet other embodiments, the angle of the pillars 52*h-m* of the second group 50 may vary in an eccentric or non-uniform manner.

Figure 10:
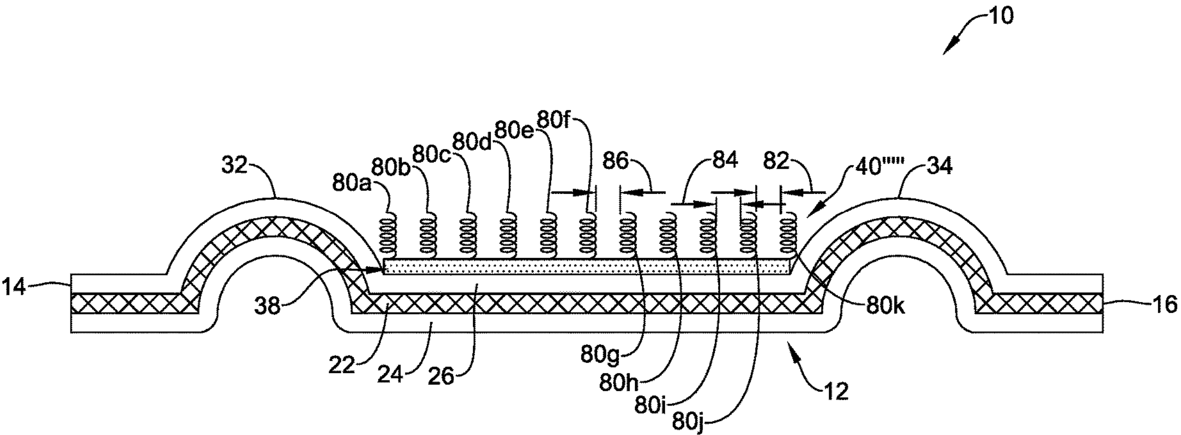
FIG. 10 is a partial schematic cross-sectional view of the illustrative stent of FIG. 1 depicting another illustrative arrangement of a plurality of pillars.

FIG. 10 illustrates a partial schematic cross-sectional view of the illustrative stent 10 depicting another illustrative arrangement of a columnar structure formed of a plurality of pillars 80*a-k* (collectively, 80) forming another illustrative macro-porous layer 40'''''. The pillars 80 may be similar in form and function to the pillars 44 described herein. The pillars 80 may extend radially from an outer surface of the inner micro-porous layer 38. While the pillars 80 are illustrated as extending generally orthogonally to a longitudinal axis of the stent 10, it is contemplated that one or more of pillars 80 may extend at a non-orthogonal angle, if so desired. In the illustrated embodiment, the pillars 80 may be deposited such that tissue growth from the two different non-adherent tissues/structures is towards one another (e.g., towards a central pillar 800. For example, the pillars 80 may have a varying longitudinal and/or circumferential spacing along the length and/or the circumference of the stent 10. While the central pillar 80*f* is illustrated as centrally located along the length of the stent 10, this is not required. In some cases, the mid-point of the pillars 80 may not correspond to the mid-point of the stent 10.

In some cases, the longitudinal and/or circumferential spacing between adjacent pillars 80 may decrease towards the centrally located pillar 80*f* such that there is a greater density of pillars 80 adjacent to the central located pillar 80*f* than near either the first or second flanges 32, 34. For example, there may be a first distance 82 between the distalmost pillar 80*k* (closer to the distal end 16) and the pillar 80*j* proximally adjacent thereto. There may be a second distance 84 between the pillar 80*j* second from the distal end and the pillar 80*i* proximally adjacent thereto. The second distance 84 may be less than the first distance 82. There may be a third distance 86 between the centrally located pillar 80*f* and the pillar 80*g* distally adjacent thereto. The third distance 86 may be less than either the first or the second distance 82, 84. The pillars 80*a*-80*e* proximal to the centrally located pillar 80*f* (e.g., closer to the proximal end 14) may have a similar spacing arrangement in which the distance between adjacent pillars 80 decreases towards the centrally located pillar 80*f*. While the spacing between pillars 80 is illustrated with respect to longitudinal spacing, it is contemplated that the circumferential spacing may also decrease towards the centrally located pillar 80*f*, although this is not required. In other examples, the longitudinal spacing may remain constant while the circumferential spacing decreases towards the centrally located pillar 80*f*. In yet other embodiments, the longitudinal and circumferential spacing of the pillars 80 may increase towards the centrally located pillar 80*f* or the pillars may be non-uniformly or eccentrically spaced.

After the stent 10 is implanted to create an anastomosis between two separate anatomical structures, tissue may grow into the void space along the macro-porous layer 40, 40', 40'', 40''', 40'''', 40''''' from one or both anatomical structures (e.g., the gallbladder and the gastrointestinal (GI) tract) to form a tissue conduit around the stent 10 from native tissue. For example, as described above, the inner micro-porous layer 38 may encourage cell attachment while the outer macro-porous layer 40 may encourage tissue ingrowth. It is further contemplated that the coating 36 may inhibit or limit a foreign body response. Inclusion of both the inner micro-porous layer 38 and the macro-porous layer 40 may encourage an anastomosis to grow from natural tissue between the gallbladder 90 and the stomach/duodenum 92 (or two other non-adherent structures/tissues) without the stent 10 migrating out of position. In some instances, the inner micro-porous layer 38 and/or the outer macro-porous layer 40 may be absorbed into the body tissue over time as the new tissue in-growth occurs. As the tissue from the two non-adherent structures grows, the tissues from each of the non-adherent structures may grow together or connect to form a tissue conduit between the non-adherent structures. In some instances, once sufficient native tissue has formed along the body 18 of the stent 10, the stent 10 may be removed, leaving the native tissue conduit as an anastomosis between the anatomical structures (e.g., the gallbladder and the gastrointestinal (GI) tract) for fluid drainage therebetween.

Figure 11A:
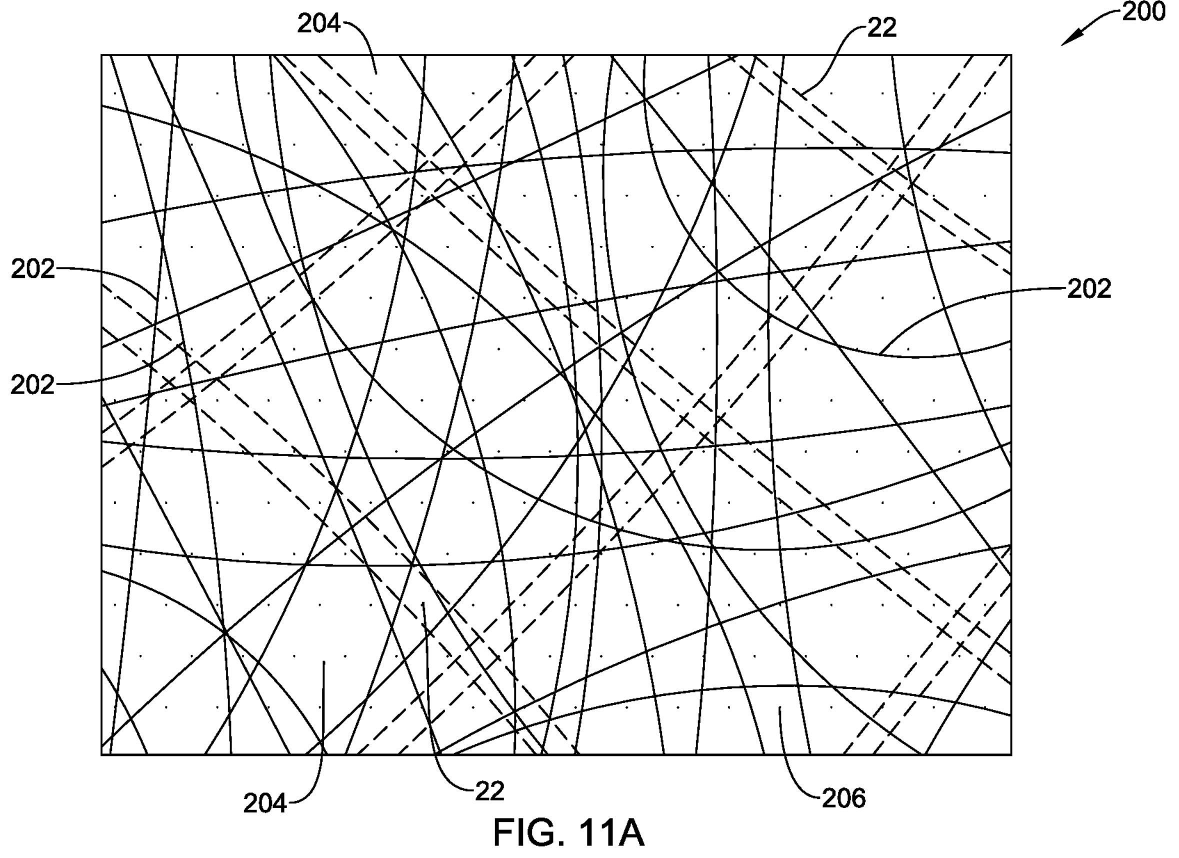
FIG. 11A is a schematic top view of an illustrative polymer matrix.

In some embodiments, the coating 36 may include a polymer matrix. FIG. 11A is a schematic top view of an illustrative polymer matrix 200. The polymer matrix 200 may include a plurality of fibers 202 defining a plurality of pores 204 (e.g., interstices). The plurality of fibers 202 may be disposed over the plurality of struts 22 and the plurality of openings 23 of the tubular member 12, (e.g., providing a porous matrix over the tubular member 12). Each fiber of the plurality of fibers 202 may have a diameter ranging from about 100 nanometers (nm) to about 900 nm, such as from about 300 nm to about 700 nm, about 230 nm to about 550 nm, or about 450 nm to about 650 nm. Each fiber 202 may have the same diameter, or the plurality of fibers 202 may include fibers of differing dimensions. It should be appreciated that the diameter(s) of the fibers 202 may be at least partially determinative of the size(s) of the pores 204 defined between adjacent fibers 202. It is further contemplated that the diameter of the fibers 202 may be at least partially determinative of the amount of tissue ingrowth that can occur through the polymer matrix 200. For example, fibers 202 having a diameter in the range of about greater than 500 nanometers (nm) may encourage tissue ingrowth while diameters less than 500 nm may cause the polymer matrix 200 to become a barrier to tissue ingrowth. The thickness of polymer matrix 200 may range from at least 1 micron (μm) to at least one millimeter (mm), such as, for example, from about 1.5 μm to about 850 μm, from about 5 μm to about 10 μm, from about 50 μm to about 250 μm, from about 350 μm to about 750 μm, from about 450 μm to about 600 μm, from about 650 μm to about 950 μm, or about 300 μm to about 550 μm. It is contemplated that the thickness of the polymer matrix 200 may be at least partially determinative of an ease of removability of the stent 10. For example, a thinner polymer matrix 200 may allow for less tissue ingrowth than a thicker polymer matrix 200. Less tissue ingrowth may increase the removability of the stent 10. Some illustrative polymer matrices may be found in commonly assigned U.S. Patent Application Publication No. 2022/0296396, published on Sep. 22, 2022, titled MEDICAL IMPLANTABLE DEVICES AND METHODS OF USING THE SAME, the disclosure of which is incorporated herein by reference.

Being porous, the polymer matrix 200 may allow passage of one or more materials through the polymer matrix 200. For example, as described in further detail herein, the polymer matrix 200 may permit tissue growth between the plurality of fibers 202 and through the plurality of pores 204. The dimensions (e.g., thickness, diameter, etc.) of the plurality of fibers 202 and/or the dimensions of the plurality of pores 204 may at least partially determine a rate of tissue growth through the polymer matrix 200. In some embodiments, the plurality of fibers 202 may be sintered to strengthen a material composition of the plurality of fibers 202 and reduce a friability of the polymer matrix 200. According to some examples herein, the porosity of the polymer matrix 200 may remain substantially consistent when sintering the plurality of fibers 202. Further, for example, the porosity of polymer matrix 200 may be fine-tuned to allow for adequate degradation and cell growth infiltration between the plurality of fibers 202 and through the plurality of pores 204.

Figure 11B:
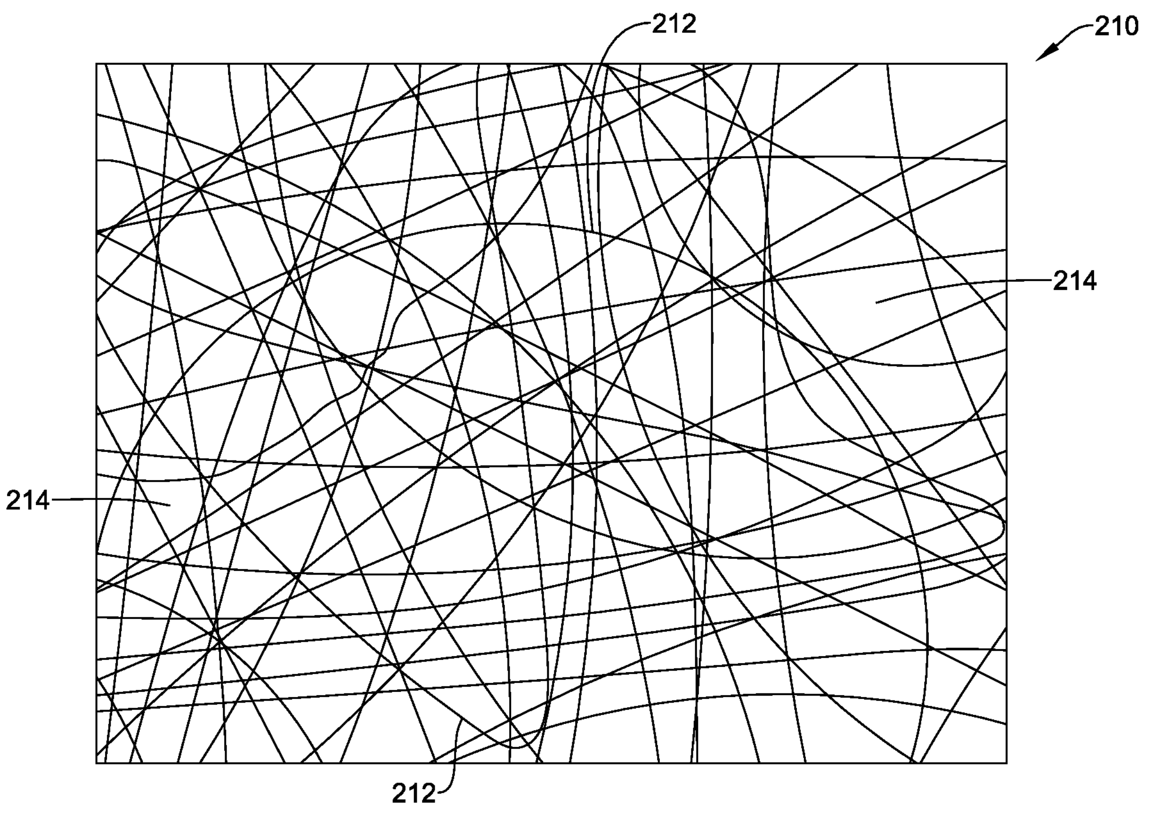
FIG. 11B is a schematic top view of another illustrative polymer matrix.

In some examples, the stent 10 may include two or more layers of the polymer matrix 200. It is contemplated that the layers may be extremely thin layers stacked one on top of the other to achieve the desired thickness. In some examples, the layers may have similar properties. For example, each layer may have a similar porosity and/or include fibers of similar dimensions. However, this is not required. In some cases, differing layers may provide different properties. FIG. 11B is a schematic top view of another illustrative polymer matrix 210. The polymer matrix 210 may include a plurality of fibers 212 defining a plurality of pores 214 (e.g., interstices). The plurality of fibers 212 may be similar in form and function to the plurality of fibers 202 described herein. It is contemplated that the density of the plurality of fibers 212 of the polymer matrix 210 may be greater than the density of the plurality of fibers 202 of the polymer matrix 200 of FIG. 11A. The density of the plurality of fibers 212 of the polymer matrix 210 of FIG. 11B may stop tissue ingrowth. It is contemplated that the polymer matrix 210 of FIG. 11B may be positioned between the stent 10 and the polymer matrix 200 of FIG. 11A. It is contemplated that positioning a denser polymer matrix 210 between a less dense polymer matrix 200 (configured to encourage tissue ingrowth) and the tubular member 12 may allow tissue ingrowth to a specified depth (e.g. the thickness of the less dense polymer matrix 200) but prevent tissue ingrowth from the reaching the struts 22 of the stent 10. In some cases, the denser polymer matrix 210 may provide a lubricious insulating layer between the target tissue and the struts 22 of the stent 10.

The polymer matrix 200 may be formed over the tubular member 12 by any suitable technique, including, for example, electrospinning. For example, a polymer material may be electro-spun over the tubular member 12 to form the polymer matrix 200. Exemplary polymer materials include, but are not limited to, thermoplastic polymers, including fluoropolymers, which may be electro-spun while in liquid solution form. The material(s) may be delivered with high electrical forces such that the material(s) may be deposited over an exterior of the tubular member 12 in a randomized, asymmetrical, and/or irregular pattern. Solvent(s) in the liquid solution may evaporate and polymer chains form, for example, becoming mechanically entangled. The resulting structure may include the plurality of fibers 202 deposited onto tubular member 12. In some embodiments, the polymer matrix 200 may comprise polyvinylidene fluoride, polyvinylidene difluoride (PVDF), and/or hexafluoropropylene (HFP).

As seen in FIG. 11A, the plurality of fibers 202 may be intertwined with one another over the plurality of struts 22. It should be appreciated that the plurality of fibers 202 may be further intertwined with an exterior surface of the tubular member 12, such as, but not limited to the inner and/or outer covering 24, 26 (if so provided) to secure the polymer matrix 200 to the tubular member 12. The plurality of fibers 202 may comingle with the material of the outer layer(s) 26. The outer layer(s) 26 may comprise a polymer, such as, for example, silicone. Accordingly, during an electrospinning process of generating the polymer matrix 200 over the tubular member 12, the material electro-spun onto the tubular member 12 (e.g., fluoropolymer) may be mechanically entangled with the outer layer 26.

The outer layer 26 may be positioned between at least a portion of the tubular member 12 and the polymer matrix 200. For example, silicone or other suitable polymer material of the outer layer(s) 26 may be disposed within at least a portion of the plurality of openings 23 between the plurality of the struts 22, and the plurality of fibers 202 may be deposited over the plurality of struts 22 and/or the plurality of openings 23. To minimize constraining a flexibility of the tubular member 12, the plurality of fibers 202 may be concentrated over the plurality of struts 22 during the electrospinning process of the polymer matrix 200. Further, the plurality of fibers 202 may be selectively guided over the plurality of struts 22 during the electrospinning process to preserve a profile of the plurality of openings 23 defined therebetween. With the polymer matrix 200 formed along an exterior of the tubular member 12, the polymer matrix 200 may provide and maintain a barrier about the lumen of tubular member 12. As described in detail herein, the polymer matrix 200 may provide a fixation mechanism for securing the stent 10 to a target treatment site within a subject. Further, the polymer matrix 200 may encourage tissue ingrowth to encourage anastomosis formation between two non-adherent tissues/structures.

The stent 10 may further include an optional bio-adhesive coating 206 disposed over, and at least partially covering, the polymer matrix 200. The bio-adhesive coating 206 may be chemically bonded to polymer matrix 200. Accordingly, the polymer matrix 200 may be disposed between the bio-adhesive coating 206 and the tubular member 12 such that the bio-adhesive coating 206 is separated from the tubular member 12 by the polymer matrix 200. The bio-adhesive coating 206 may comprise a biodegradable material, such that the bio-adhesive coating 206 may be resorbed or otherwise degrade after a period of time. The bio-adhesive coating 206 may maintain contact with a target treatment site (e.g., tissue) for a desired amount of time, which may depend on chemical characteristics and/or the thickness of the bio-adhesive coating 206. For example, the bio-adhesive coating 206 may maintain contact with the target treatment site from approximately 24 hours to approximately 6 months, such as from about 3 days to about 1 week, from about 1 week to about 6 weeks, from about 1 month to about 3 months, or about 2 months to about 5 months. The degradation time may be controlled by various factors, including, for example, the nature of the biodegradable material and/or quantity (e.g., thickness) of the bio-adhesive coating 206 on polymer matrix 200. The thickness of the bio-adhesive coating 206 over polymer matrix 200 may range from about at least 1 μm to at least 1 mm, such as, e.g., from about 1.5 μm to about 850 μm, from about 5 μm to about 10 μm, from about 50 μm to about 250 μm, from about 350 μm to about 750 μm, from about 450 μm to about 600 μm, from about 650 μm to about 950 μm, or about 300 μm to about 550 μm. Further, the bio-adhesive coating 206 may be chemically modified on an exterior surface of polymer matrix 200.

Illustrative materials suitable for the bio-adhesive coating 206 may include, but are not limited to, polysaccharides such as chitosan. The polysaccharide may be crosslinked with a linker molecule. Such linker molecules include, for example, polyethylene glycol (PEG). In some cases, 1-ethyl-3-(-3-dimethylaminopropyl) carbodiimide hydrochloride (EDC) may be added to bind the chitosan and the PEG. PEG may provide a hydrophilic scaffold along the polymer matrix 200, and may serve as an anchor for the bio-adhesive coating 206 to attach to polymer matrix 200. The hydrophilic properties of PEG may provide adhesive capabilities for securing the bio-adhesive coating 206 to the polymer matrix 200. Other suitable materials for the bio-adhesive coating 206 may include, but are not limited to, polymers such as chitosan optionally modified with thiol groups, PEG modified with thiol groups, and oxidized cellulose. The bio-adhesive coating 206 may have hemostatic properties for stimulating a healing response from a target treatment site (e.g., tissue) when in contact thereto. Stated differently, the bio-adhesive coating 206 may treat injuries at the target treatment site, such as wounds, hemorrhages, damaged tissues, bleeding, etc. The bio-adhesive coating 206 may serve as a wound dressing to inhibit excessive bleeding and/or promote rapid healing. Additionally, the bio-adhesive coating 206 may have adhesion characteristics capable of securing tubular member 12 to the target treatment site. For example, in some cases, the bio-adhesive coating 206 may have a positive charge, complementary to a negative charge of the mucous layer of the body. In some cases, the bio-adhesive coating 206 may be desiccated which may further increase the attraction between the bio-adhesive coating 206 and the hydrated mucous layer.

As mentioned above, the bio-adhesive coating 206 may be chemically bonded to the polymer matrix 200, including via the linker molecule. Accordingly, the linker molecule (e.g., PEG) may be cross-linked with the plurality of fibers 202 to facilitate a connection between the bio-adhesive coating 206 and the polymer matrix 200. In some examples, the linker molecule may become entangled with the polymer chains of the polymer matrix 200 as the plurality of fibers 202 are formed on tubular member 12. In some examples, the bio-adhesive coating 206 may be prepared using plasma to cross-link the polysaccharide and linker molecule. The bio-adhesive coating 206 may provide a temporary fixation mechanism for securing the stent 10 to a target treatment site within a subject.

According to some aspects of the present disclosure, the plurality of fibers 202 may be selectively deposited over the tubular member 12 to control a fixation characteristic of the stent 10 to a target treatment site and/or other characteristics of the stent 10. For example, the plurality of fibers 202 may be deposited along one or more regions of the tubular member 12, thereby controlling an area of tissue ingrowth into the stent 10 to the one or more specific regions. As discussed above, the bio-adhesive coating 206 may adhere to a surface area of the polymer matrix 200, such that the stent 10 may include the bio-adhesive coating 206 along the one or more regions of the tubular member 12 when the plurality of fibers 202 are selectively deposited thereon. In other examples, the thickness and/or regions of deposit of the polymer matrix 200 and/or the bio-adhesive coating 206 may be strategically placed to reduce bleeding and/or irritation at the implant site. For example, in some embodiments, the first and/or second enlarged regions 32, 34 may create bleeds and/or tissue irritation at the implant site. It is contemplated that increasing the thickness of the polymer matrix 200 and/or the bio-adhesive coating 206 at the first and/or second enlarged regions 32, 34 may reduce the friction between the first and/or second enlarged regions 32, 34 and the tissue thus reducing irritation of the tissue. It is further contemplated that the thickness and/or location on the tubular member 12 of the polymer matrix 200 and/or the bio-adhesive coating 206 may be tailored to a specific implant location.

Generally, the stent 10 may be positioned at the target treatment site through use of a medical instrument (e.g., an endoscope, catheter, etc.) that is inserted through the subject's body and navigated toward the target treatment site. It should be understood that the stent 10 may be used in various locations (target treatment sites) within a subject's body, including but not limited to, the gastrointestinal tract, an organ, or other tissue. Upon reaching the implant location, the stent 10 may be inserted through the medical instrument and deployed therefrom at the target location. In some embodiments, if so provided, the bio-adhesive coating 206 may provide a smooth, outer atraumatic surface to facilitate passage of the stent through the subject and/or inhibit injury to the target location by the polymer matrix 200 and/or the tubular member 12.

The stent 10 may be pressed against the target location such that the bio-adhesive coating 206 contacts the mucous layer or other tissue membrane. With tubular member 12 having a flexible configuration, the stent 10 may conform to a profile of the target location. Further, with the bio-adhesive coating 206 being positively charged and the mucous layer or other tissue membrane being negatively charged, the bio-adhesive coating 206 may be attracted to the mucous layer and form chemical bonds with the tissue surface, thereby anchoring the stent 10 to the target location. The bio-adhesive coating 206 may maintain the stent against the target location for at least a minimum duration until the bio-adhesive coating 206 is resorbed or otherwise degrades. Accordingly, the bio-adhesive coating 206 may serve a tissue adhesive mechanism for temporarily fixing the stent 10 to the target location, and inhibiting migration of the stent 10 from the target treatment site. Further, the bio-adhesive coating 206 may further promote healing of the target location via the hemostatic properties of the bio-adhesive coating 206 while the bio-adhesive coating 206 remains in contact with the target location.

As the bio-adhesive coating 206 adheres the stent 10 to the target location, the bio-adhesive coating 206 may facilitate tissue growth from the tissue wall through polymer matrix 200. Stated differently, by maintaining polymer matrix 200 within close proximity to the tissue wall, the bio-adhesive coating 206 may allow tissue cells from the tissue wall to grow through the bio-adhesive coating 206 and into the plurality of pores 204. The tissue cells may become intertwined with the plurality of fibers 202, thereby anchoring the stent 10 to the tissue wall and inhibiting migration of the stent from the target treatment site. In other words, the plurality of pores 204 may serve as sites that permit tissue growth into the polymer matrix 200. The bio-adhesive coating 206 may maintain the stent 10 against the tissue wall via bonding with the mucous layer or other tissue membrane, to thereby allow the tissue cells sufficient time to grow through the polymer matrix 200.

As described further above, the size(s) of the plurality of pores 204 may at least partially control the rate of tissue cell growth through the polymer matrix 200, and the diameter(s) of the plurality of fibers 202 may at least partially determine the size(s) of the plurality of pores 204. Further, the diameter (s) of the plurality of fibers 202 may correspond or correlate to a minimum required force for disengaging the stent 10 from a target treatment site. Stated differently, the plurality of fibers 202 may be sized and/or shaped to provide the stent sufficient mechanical strength in inhibiting migration of the stent 10 from the target treatment site. For example, a minimum extraction force sufficient to move the stent 10 relative to the target treatment site may be at least partially associated with a size and/or shape of the plurality of fibers 202. Accordingly, the diameter of the plurality of fibers 202 may at least partially contribute to inhibiting the unintentional release of the stent 10 from the target tissue.

Upon degradation of the bio-adhesive coating 206, the stent 10 may remain anchored to the tissue wall via an engagement of the polymer matrix 200 to the target tissue (e.g., tissue ingrowth into the polymer matrix 200). Accordingly, despite removal of the bio-adhesive coating 206 from between polymer matrix 200 and the target tissue, the polymer matrix 200 and the tubular member 12 may remain attached to the target tissue in response to the tissue cell growth through the polymer matrix 200. By providing a physical barrier between tubular member 12 and the target tissue, the polymer matrix 200 may ensure a fluid pathway through tubular member 12 is preserved. Further, the polymer matrix 200 may facilitate removal of the stent 10 upon completion of a procedure. For instance, the polymer matrix 200 may reduce a surface area of tubular member 12 which may be anchored to the target tissue, thereby allowing the stent 10 to be removed from the subject upon applying an application of force thereto. Further, for example, the thickness of stent 10 including the thickness of the polymer matrix 200 and an exposed portion of the plurality of fibers 202 may facilitate removal of the stent 10 from the subject. Additionally, the polymer matrix 200 may control an extent (e.g., depth) and/or degree of tissue ingrowth into the stent, providing further control for the removal of the stent 10 upon completion of a procedure. For example, as described above, in some cases, an inner layer of polymer matrix 210 may be provided to limit a depth of tissue ingrowth.

Figure 12:
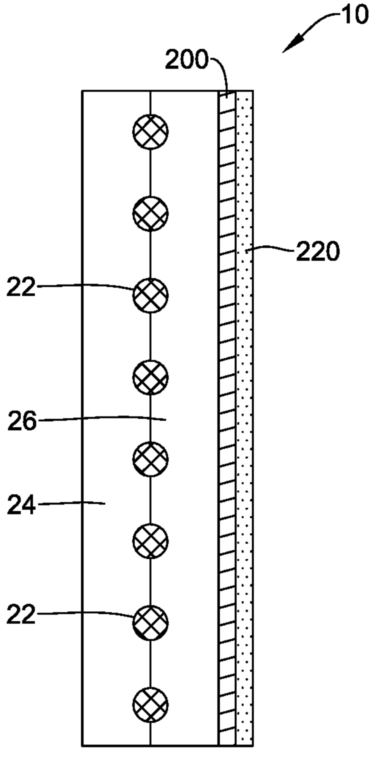
FIG. 12 is an enlarged cross-sectional view of a portion of the illustrative stent of FIG. 2 having an alternative coating.

In some embodiments, alternative materials may be used in place of the bio-adhesive coating with or without the polymer matrix 200. FIG. 12 an enlarged cross-sectional view of a portion of the illustrative stent 10 having an alternative coating 220. While the stent 10 is illustrated as including an inner layer 24, an outer layer 26, and a polymer matrix 200, it is contemplated that any one, any two, or all of these layers may be omitted. In some cases, the alternative coating 220 may be a hydrogel adhesive layer. Some illustrative hydrogels mays include, but are not limited to, gelatin, gelatin methacryloyl (GelMA), polyethylene glycol (PEG) based bio-adhesives, chitosan, and/or their derivatives. It is contemplated that a hydrogel adhesive layer may reduce the foreign body response. In some cases, the hydrogel may be attracted to the mucous layer (or other body tissue) to facilitate attachment of the stent 10 at the target location and limit migration of the stent 10 after implantation. In some cases, the hydrogel may be configured to maintain the stent 10 in the implant location for a desired period of time. For example, the hydrogel may be configured to maintain the stent 10 in the desired location until tissue ingrowth has penetrated the struts 22 and/or polymer matrix 200, if so provided.

In another example, the alternative coating 220 may be a filler hemostatic agent. Some illustrative hemostatic agents may include, but are not limited to, kaolin and sodium montmorillonite (MMT). The hemostatic agent may have some bio-adhesive properties which allow the hemostatic agent to at least temporarily adhere to the body tissue after implantation. In some cases, the hemostatic agent may be configured to maintain the stent 10 in the implant location for a desired period of time. For example, the hemostatic agent may be configured to maintain the stent 10 in the desired location until tissue ingrowth has penetrated the struts 22 and/or polymer matrix 200, if so provided. In some examples, the hemostatic agent may be provided as a coating disposed over the polymer matrix 200, as shown in FIG. 12.

In other examples, the hemostatic agent may be blended into the electrospinning polymer solution to impart hemostatic and bio-adhesive properties directly to the polymer matrix 200. In such at instance, the polymer matrix 200 may form the outermost layer of the stent 10.

Figure 13:
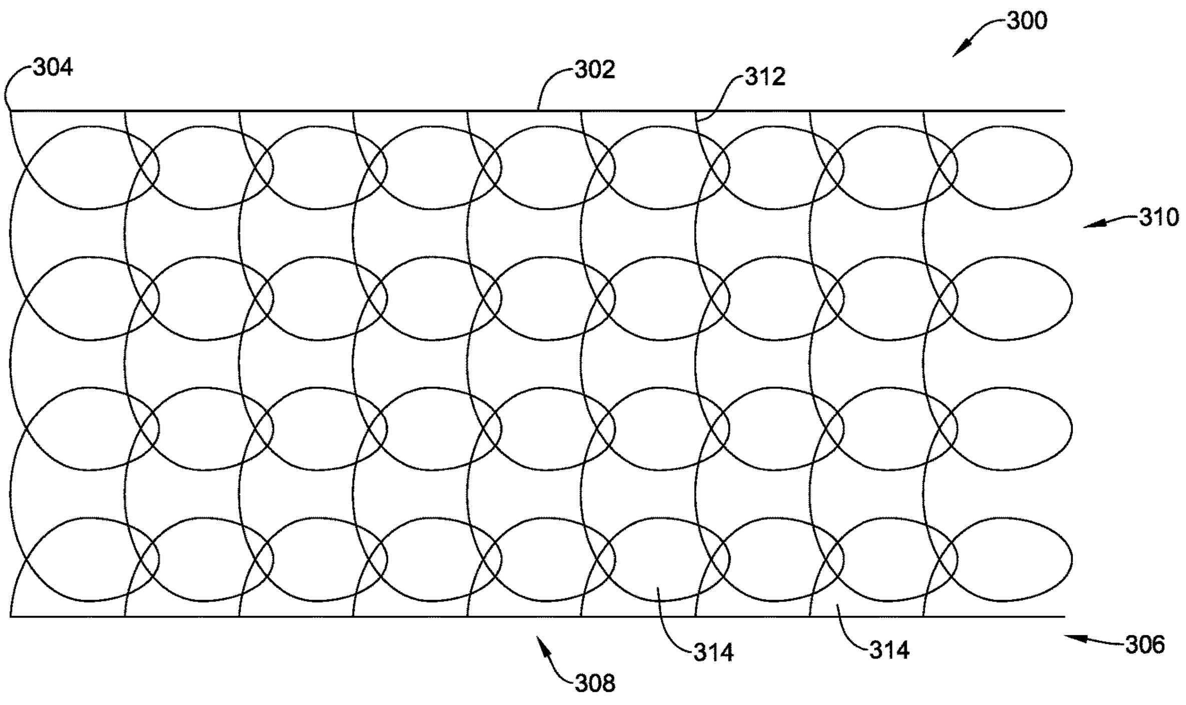
FIG. 13 is a side view of an illustrative outer layer for use with a stent.

FIG. 13 is a side view of another illustrative outer mesh or fabric sleeve 300 for use with a stent, such as the stent 10 described herein. In some instances, the outer mesh or fabric sleeve 300 may be formed from an elongated tubular member 302. While the outer mesh or fabric sleeve 300 is described as generally tubular, it is contemplated that the outer mesh or fabric sleeve 300 may take any cross-sectional shape desired. For example, the outer mesh or fabric sleeve 300 may be shaped to fit over or conform to one or more portions of the stent 10, including the flanges 32, 34. The outer mesh or fabric sleeve 300 may be configured to extend over an entire length of the stent 10 or only a portion of the length thereof. For example, in some instances, the outer mesh or fabric sleeve 300 may extend along the body 18 of the stent 10, but not extend over the flanges 32, 34. Thus, the entire length of the outer mesh or fabric sleeve 300 may be positioned between the flanges 32, 34. In some cases, the outer mesh or fabric sleeve 300 may be provided as two or more discrete components with each of the two or more discrete components configured to be positioned over a different portion of the stent 10 with some, little, or no overlap between the discrete components. In some cases, the outer mesh or fabric sleeve 300 may be fixedly coupled to the stent 10. In other cases, the outer mesh or fabric sleeve 300 may be positioned over, but free from coupling to the stent 10. For example, the outer mesh or fabric sleeve 300 may float over the outer surface of the stent 10 such that the outer mesh or fabric sleeve 300 may move axially and/or circumferentially relative to the stent 10.

The outer mesh or fabric sleeve 300 may have a first, or proximal end 304, a second, or distal end 306, and an intermediate region 308 disposed between the first end 304 and the second end 306. The outer mesh or fabric sleeve 300 may include a lumen 310 extending from a first opening adjacent the first end 304 to a second opening adjacent to the second end 306 to allow for outer mesh or fabric sleeve 300 to be positioned over the stent 10.

The outer mesh or fabric sleeve 300 may be expandable from a first radially collapsed configuration (not explicitly shown) to a second radially expanded configuration with the expansion of the stent 10. In some cases, the outer mesh or fabric sleeve 300 may be deployed to a configuration between the collapsed configuration and a fully expanded configuration.

The outer mesh or fabric sleeve 300 may have an interwoven (e.g., knitted) structure, fabricated from a single filament 312 interwoven with itself and defining open cells 314 or multiple filaments interwoven (e.g., braided) with each other. In some cases, the filament(s) 312 may be a monofilament, while in other cases the filament(s) 312 may be two or more filaments wound, braided, or woven together. While the illustrated embodiment illustrates a twisted knit stitch, it is contemplated that the outer mesh or fabric sleeve 300 may be formed using any stitch desired. Further, the outer mesh or fabric sleeve 300 may be formed using other techniques, including, but not limited to, weaving or winding. When the stent 10 is positioned in the body at the target location, the The plurality of open cells 314 may allow for ingrowth of tissue about the filament 312. It is contemplated that an amount of tissue ingrowth may be controlled by a tightness of the knit. For example, the outer mesh or fabric sleeve 300 may be formed such that that the open cells 314 are very small (e.g., adjacent portions of the filament 314 contact or nearly contact). In other examples, the outer mesh or fabric sleeve 300 may be formed with a looser knit such that adjacent portions of the filament 314 are spaced from one another to form larger cells 314. The larger the cells 314, the greater the tissue ingrowth may be. Sufficient tissue ingrowth into and along the outer mesh or fabric sleeve 30 may form a tissue conduit connecting two separate anatomical structures, forming an anastomosis therebetween. In some instance, once the tissue ingrown in the outer mesh or fabric sleeve 300 has sufficiently formed a tissue conduit between the anatomical structures, the stent 10 may be removed, leaving the outer mesh or fabric sleeve 300 in place at the formed anastomosis.

It is contemplated that the outer mesh or fabric sleeve 300 can be made from a number of different materials such as, but not limited to, synthetic or bio-absorbable textile materials. Some illustrative synthetic textile materials may include, but are not limited to, polyamide, polyester, polyethylene terephthalate (PTFE), expanded PTFE, polypropylene (PP), etc. Some illustrative bio-absorbable textile materials may include, but are not limited to poly(glycolic acid) (PGA), polylactic acid (PLA), poly (L-lactide) (PLLA), poly(lactic-co-glycolic acid) (PLGA), polydioxanone (PDO), etc.

It is contemplated that any of the inner or outer layers 24, 26, coatings/layers 36, 38, 40, 40', 40", 40', 40"", 40'"", polymer matrix 200, 210, bio-adhesive coating 206, alternative outer coating 220, and/or the outer mesh or fabric sleeve 300 may be disposed over all or select portions of the stent 10. In comes cases, the location and/or thickness of the inner or outer layers 24, 26, coatings 36, 38, 40, 40', 40", 40'" 40", 40'"" polymer matrix 200, 210, bio-adhesive coating 206, alternative outer coating 220, and/or the outer mesh or fabric sleeve 300 may be placed to reduce bleeding and/or tissue irritation. In some cases, the inner or outer layers 24, 26, coatings 36, 38, 40, 40', 40", 40'" 40"", 40'"", polymer matrix 200, 210, bio-adhesive coating 206, alternative outer coating 220, and/or the outer mesh or fabric sleeve 300 may be thicker at regions of the stent 10 that may be more likely to cause a bleed and/or tissue irritation upon implantation in the body, including but not limited to the flanges 32, 34. It is further contemplated that any of the inner or outer layers 24, 26, coatings 36, 38, 40, 40', 40", 40'", 40"", 40'"", polymer matrix 200, 210, bio-adhesive coating 206, alternative outer coating 220, and/or the outer mesh or fabric sleeve 300 may be applied as a plurality of layers. The number of layers may be varied to achieve the desired coating thickness.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A stent, comprising:

an elongated tubular body having a scaffolding forming a plurality of cells; and a coating disposed over an outer surface of the elongated tubular body, the coating comprising:

a first micro-porous layer; and a macro-porous layer disposed over the micro-porous layer.

2. The stent of claim 1, wherein the macro-porous layer includes a columnar structure.

3. The stent of claim 1, further comprising a second micro-porous layer disposed over the macro-porous layer.

4. The stent of claim 1, wherein the first micro-porous layer has interconnected pores in a range of about 0.05 micrometers to about 2 micrometers.

5. The stent of claim 4, wherein the macro-porous layer has a thickness in a range of at least 1 micron to at least one millimeter.

6. The stent of claim 1, wherein the first micro-porous layer has a thickness in a range of about 10 micrometers to about 80 micrometers.

7. The stent of claim 6, wherein the first micro-porous layer has interconnected pores in a range of about 0.05 micrometers to about 2 micrometers, and the macro-porous layer has a thickness in a range of at least 1 micron to at least one millimeter.

8. A stent, comprising:

an elongated tubular body having a scaffolding forming a plurality of cells; and a coating disposed over an outer surface of the elongated tubular body, the coating comprising:

a first micro-porous layer; and a macro-porous layer disposed over the micro-porous layer;

wherein the macro-porous layer includes a plurality of loops.

9. The stent of claim 8, wherein the plurality of loops are stacked one on top of another to form a plurality of pillars.

10. The stent of claim 9, wherein the plurality of pillars extend radially from an outer surface of the first micro-porous layer.

11. The stent of claim 9, wherein at least some of the plurality of pillars have a longitudinal axis extending at an oblique angle to a longitudinal axis of the elongated tubular body.

12. The stent of claim 9, wherein at least some of the plurality of pillars have a free end that is oriented towards a longitudinally centrally located pillar.

13. The stent of claim 9, wherein a density of the plurality of pillars increases towards a longitudinally centrally located pillar.

14. The stent of claim 8, wherein a loop of the plurality of loops is at least partially laterally spaced from a preceding loop.

15. The stent of claim 8, wherein each loop of the plurality of loops includes a loop portion of a filament and an overlapping base portion of the filament.

16. The stent of claim 15, wherein the overlapping base portion includes a first segment of the filament that overlaps a second segment of the filament.

17. The stent of claim 8, wherein adjacent loops of the plurality of loops are free from contact with one another.

18. The stent of claim 8, wherein the macro-porous layer comprises one or more circumferentially extending rows of the plurality of loops.

19. The stent of claim 8, wherein the macro-porous layer comprises one or more longitudinally extending rows of the plurality of loops.

20. The stent of claim 8, wherein the macro-porous layer comprises a first layer and a second layer disposed over the first layer, each of the first and second layers comprising a plurality of rows of the plurality of loops.

* * * * *